United States Patent
Kehrel et al.

(10) Patent No.: US 7,388,075 B2
(45) Date of Patent: Jun. 17, 2008

(54) MEDICAMENT CONTAINING ACTIVATED ANTITHROMBIN III

(75) Inventors: Beate Kehrel, Münster (DE); Martin Brodde, Münster (DE)

(73) Assignee: Hamburger Stiftung zur Förderung von Wissenschaft und Kultur c/o MERA GmbH, Hamburg (DE)

( * ) Notice: Subject to any disclaimer, the term of this patent is extended or adjusted under 35 U.S.C. 154(b) by 0 days.

(21) Appl. No.: 10/380,274

(22) PCT Filed: Sep. 12, 2001

(86) PCT No.: PCT/EP01/10541

§ 371 (c)(1),
(2), (4) Date: Aug. 8, 2003

(87) PCT Pub. No.: WO02/22150

PCT Pub. Date: Mar. 21, 2002

(65) Prior Publication Data

US 2004/0029799 A1 Feb. 12, 2004

(30) Foreign Application Priority Data

Sep. 12, 2000 (DE) .............................. 100 45 047

(51) Int. Cl.
*C07K 14/00* (2006.01)
(52) U.S. Cl. ...................................... 530/350
(58) Field of Classification Search ................. 524/12; 424/94, 64, 423; 532/105; 530/350; 536/21, 536/122; 514/921
See application file for complete search history.

(56) References Cited

U.S. PATENT DOCUMENTS 6,692,931 B1 * 2/2004 Reutter et al. .................. 435/13

FOREIGN PATENT DOCUMENTS

| EP | 0 326 014 A1 | 8/1989 |
| EP | 1 027 894 A2 | 8/2000 |
| WO | WO 02/058638 A2 | 8/2002 |
| WO | WO 00/29657 | * 5/2005 |

OTHER PUBLICATIONS

Bruce et al., Thromboembolic disease due to themolabile conformational changes of antithrombin Rouen-VI (187 Asn-Asp), J. clin. Invest., Dec. 1994, vol. 94, pp. 2265-2274.*

Iregui et al., Clinical importance of delays in the initiation of appropriate antibiotic treatment of ventilator-associated pneumonia, Jul. 2002, Clinical investigations in critcal care, vol. 122, pp. 263-268.*

Van Patten et al., Oxidation of methionine residues in antithrombin. Effects on biological activity and heparin binding, J Biol Chem. Apr. 9, 1999;274(15):10268-76.*

Sun et al., Re-formation of disulphide bonds in reduced antithrombin III, Biochem J. Aug. 1, 1990;269(3):665-9.☐☐.*

(Continued)

*Primary Examiner*—Robert B. Mondesi
(74) *Attorney, Agent, or Firm*—Rothwell, Figg, Ernst & Manbeck p.c.

(57) ABSTRACT

The invention concerns the use of antithrombin III with a modified conformation which is referred to as activated antithrombin III (IDAAT=immune defence activated antithrombin) as a medicament.

6 Claims, 32 Drawing Sheets

OTHER PUBLICATIONS

Figure 11:
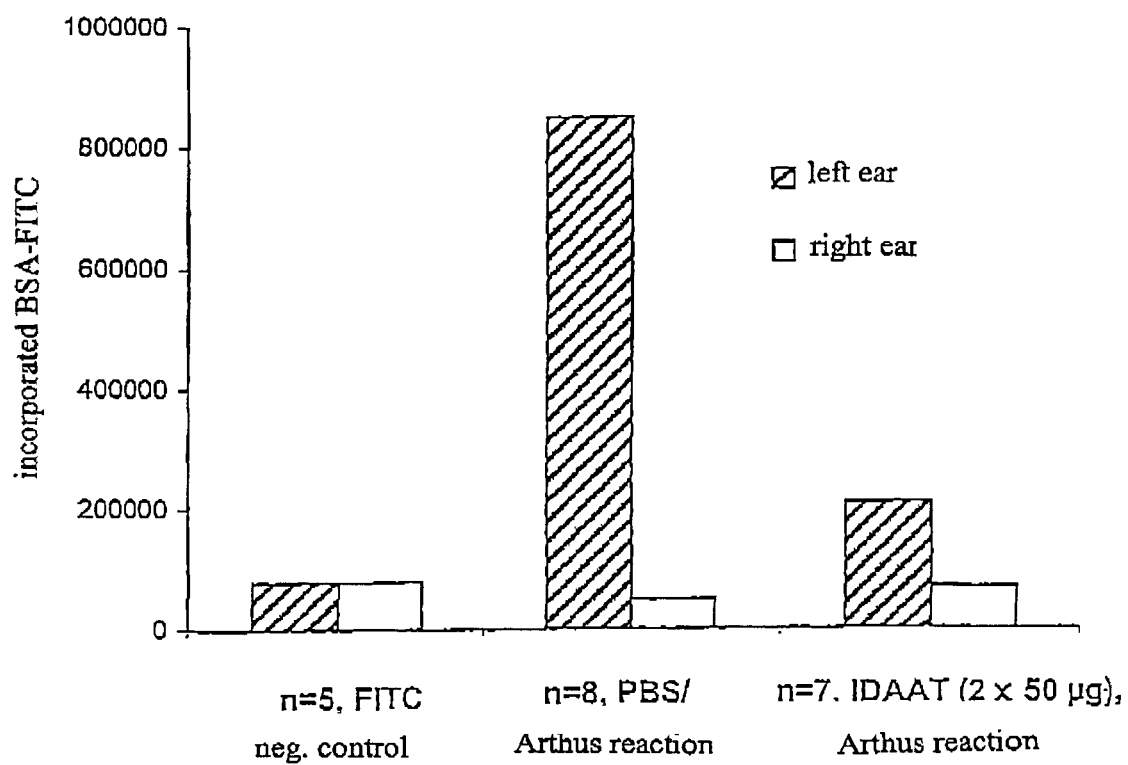

O'Reilly M S et al, "Antiangiogenic Activity of the Cleaved Conformation of the Serpin Antithrombin", Science, AAAS. vol. 285, 17, Sep. 1999, pp. 1926-1928.

Dickneitte Gerhard et al., "Reduction of Mortality with Antithrombin III in septicemic rats: A study of Klebsiella pneumoniae induced sepsis", Thrombosis and Haemostasis, vol. 69, No. 2, 1993, pp. 98-102.

Database WPI, Section Ch, Week 199730, Derwent Publication Ltd., London, GB; Class B04 AN 1997-328454 & JP 09 132534 A, May 20, 1997.

Cao Yihai, "Endogenous Angiogenesis inhibitors and their therapeutic implicatons", International Journal of Biochemistry & Cell Biology, vol. 33, No. 4, Apr. 2001, pp. 357-369.

* cited by examiner

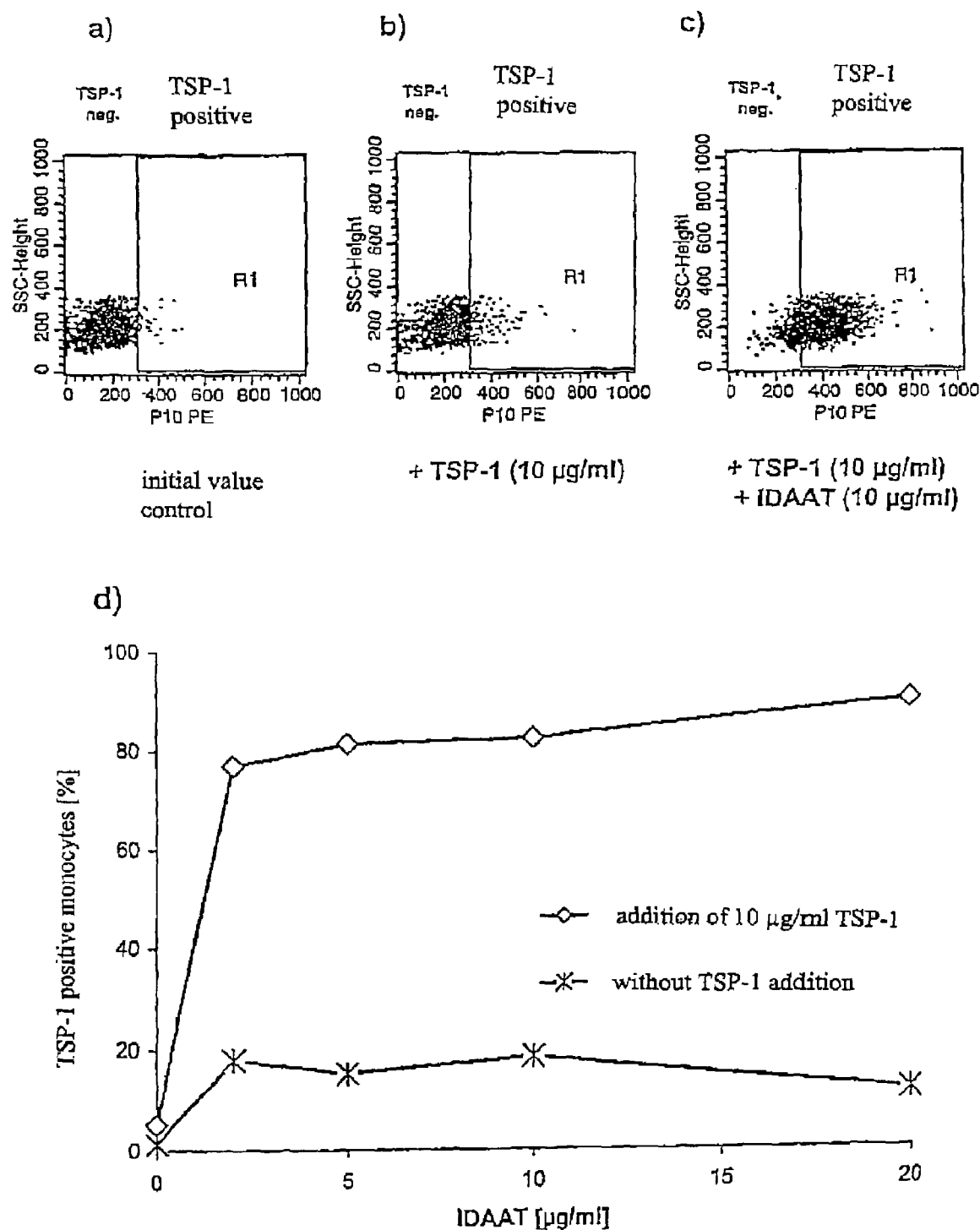
Fig. 1: IDAAT mediates TSP-1 binding to monocytes

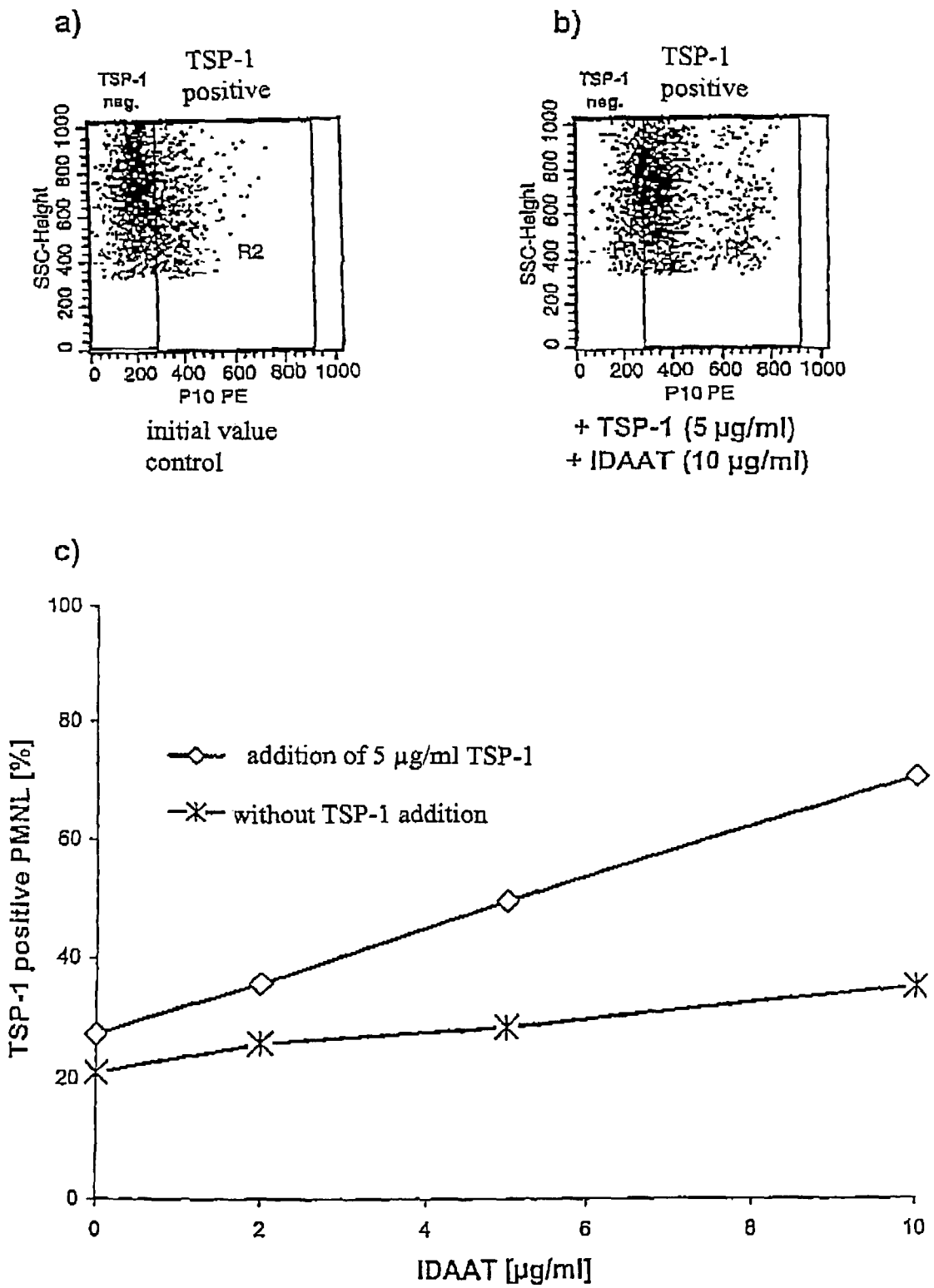
Fig.2: IDAAT mediates TSP-1 binding to apoptotic PMNL

Fig. 3: IDAAT cross-links apoptotic PMNL with monocytes by TSP
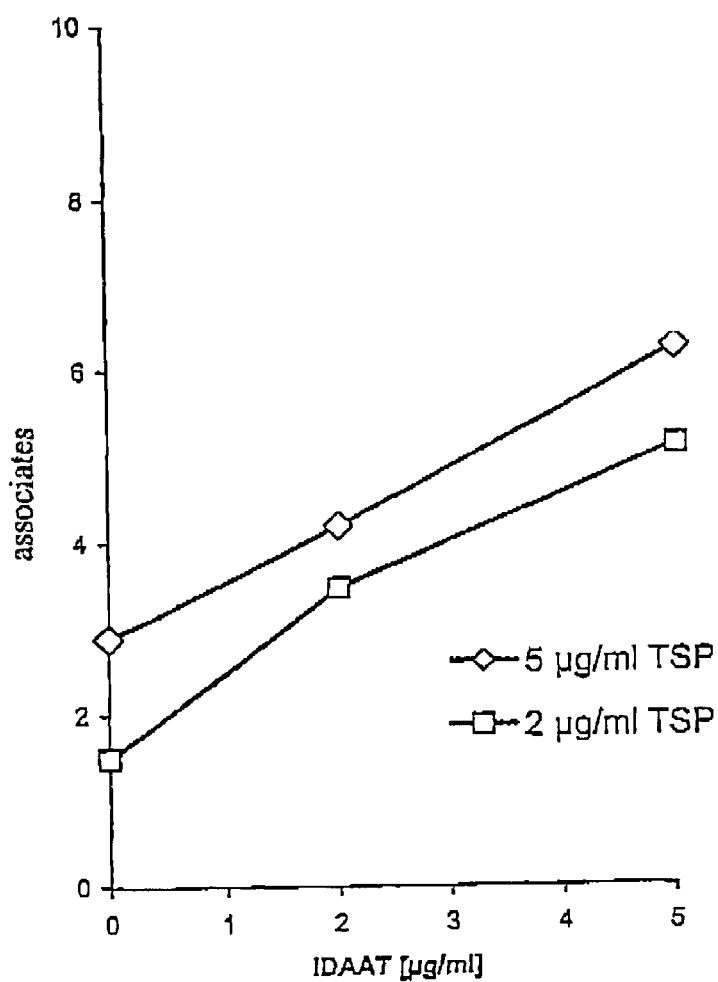

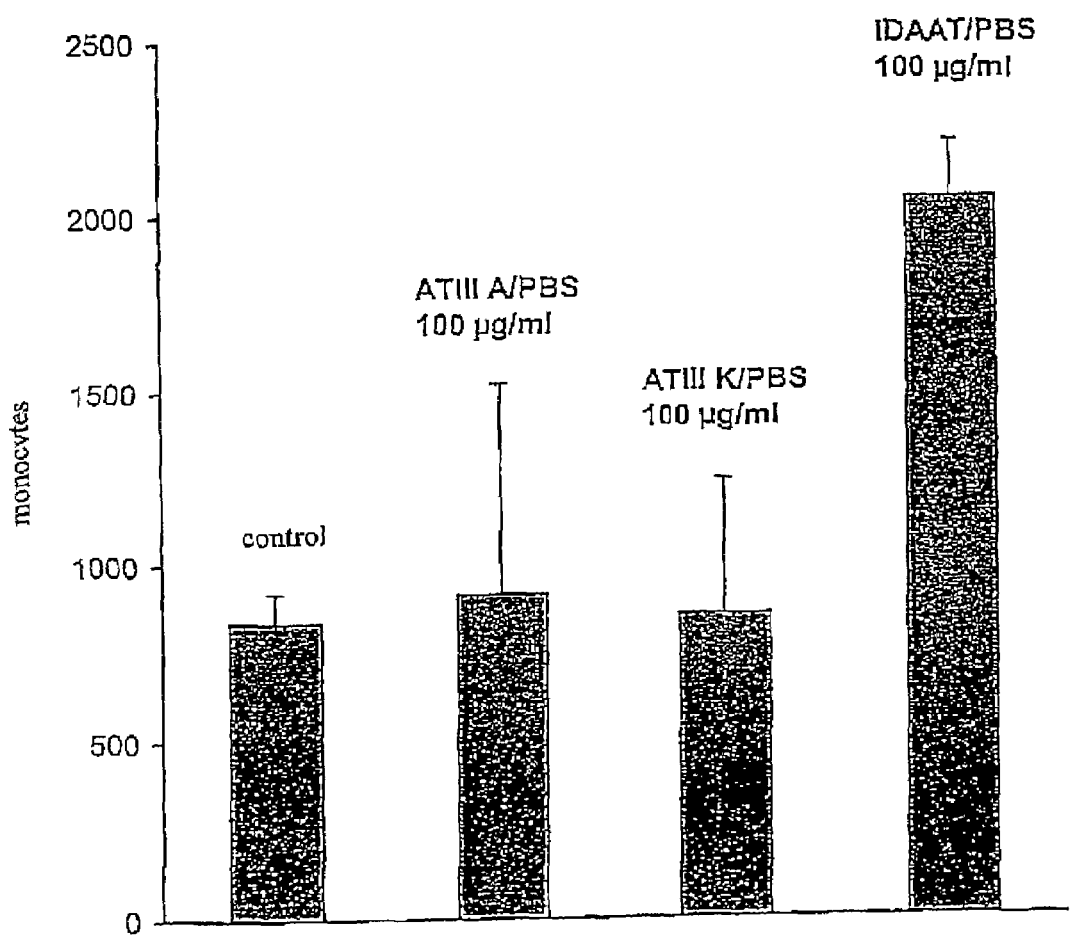
Fig. 4: Influence of IDAAT and commercial ATIII preparations on the transmigration of monocytes through a HMEC-1 monolayer Fig. 5    IDAAT induces a Ca²⁺ signal in thrombocytes
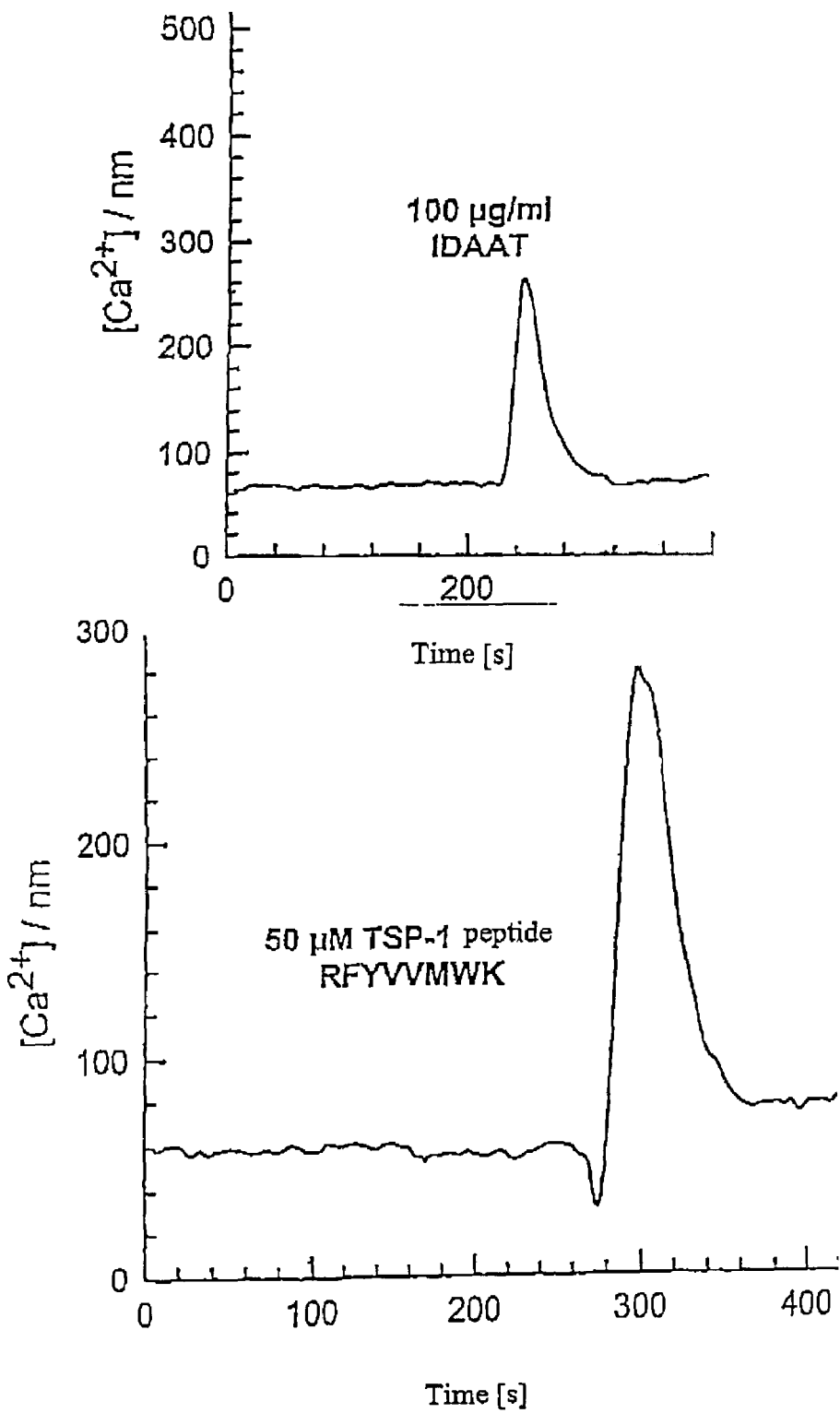

Fig. 6: IDAAT mediates the binding of TSP-1 to T cells
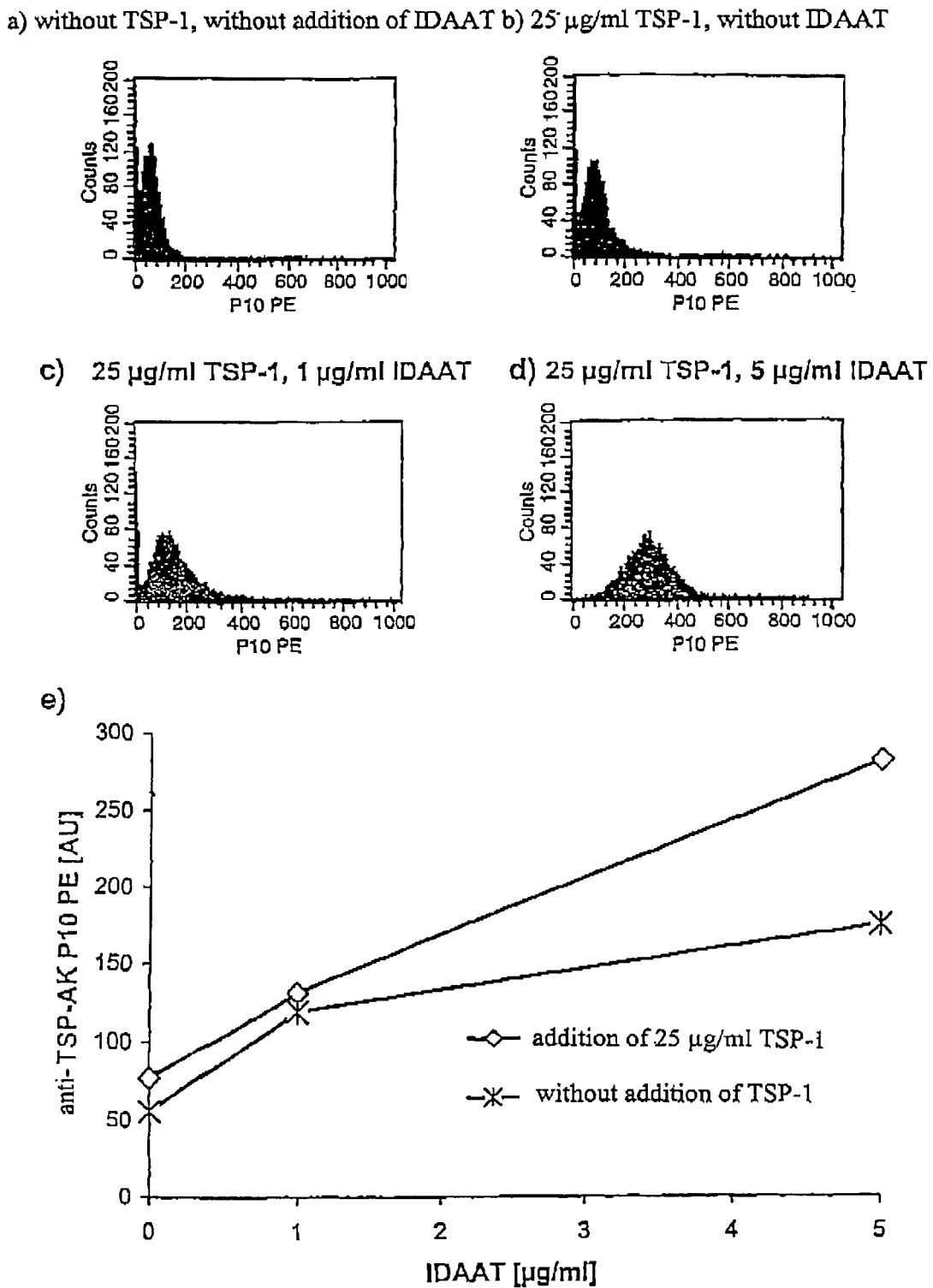

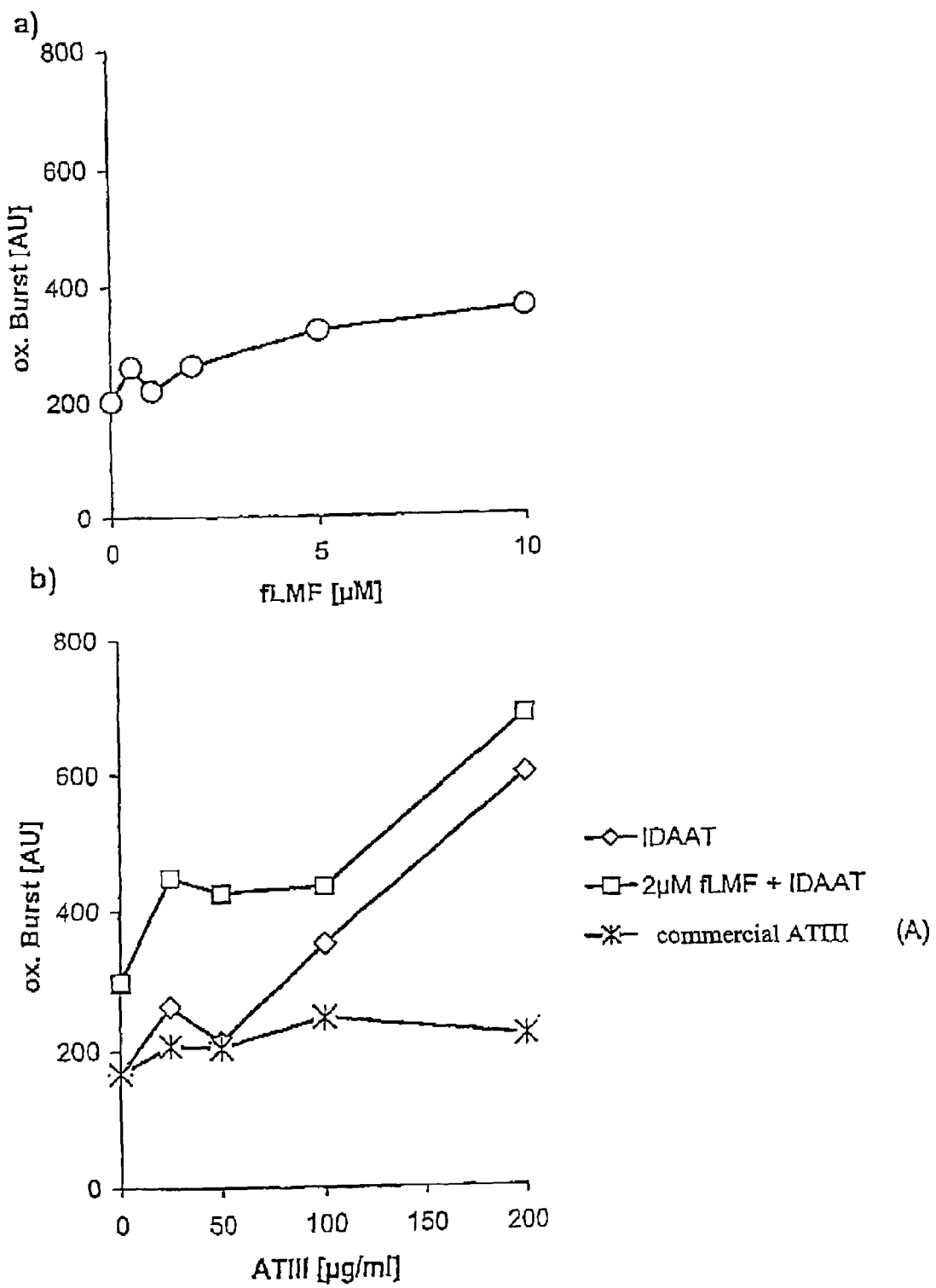
Fig. 7: IDAAT increases the activating effect of fLMF on the oxidative burst of PMNL

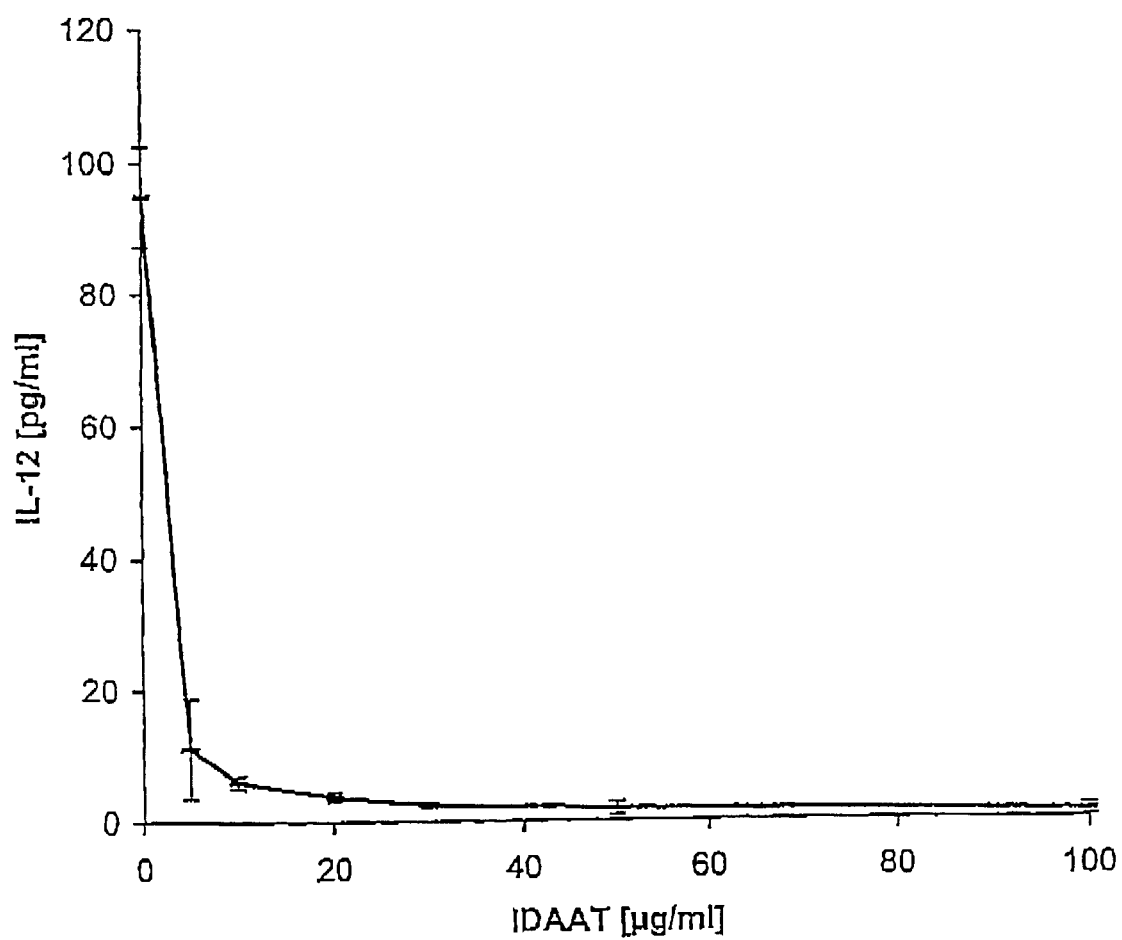
Fig. 8: IDAAT inhibits the release of active interleukin 12 (IL-12) by monocytes activated with interferon γ + S. aureus

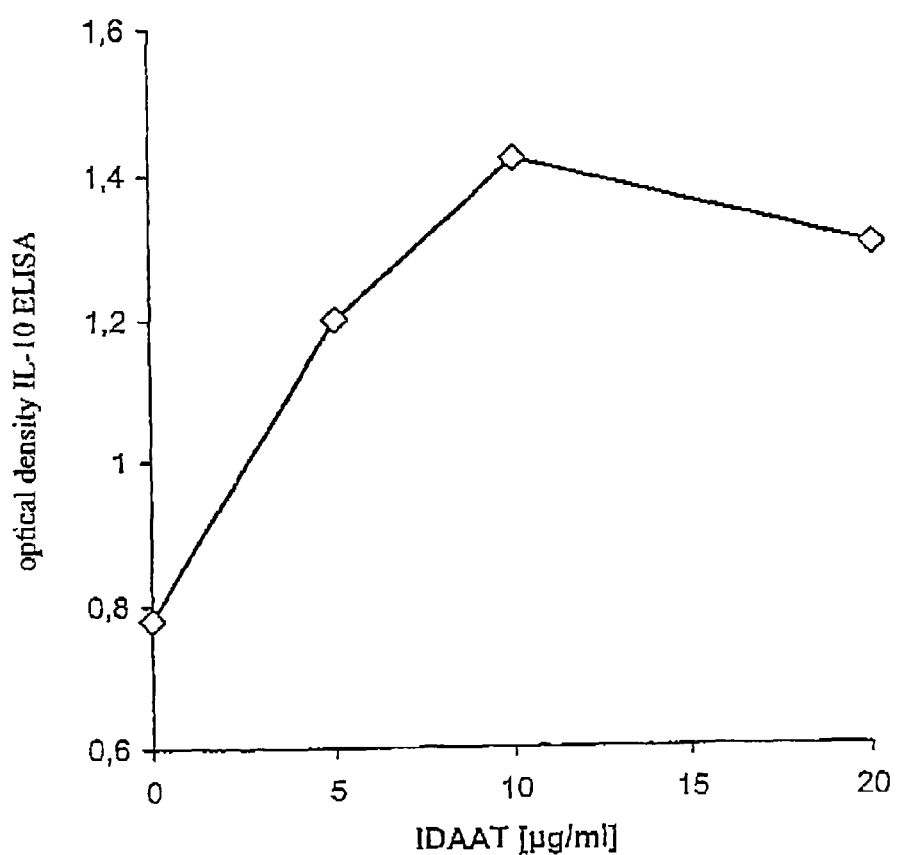
Fig. 9: IDAAT increases the IL-10 secretion of monocytes activated by S. aureus and interferon gamma Fig. 10: IDAAT increases the inhibition of the TNF alpha secretion of activated monocytes by the TSP-1 peptide RFYVVMWK
a)
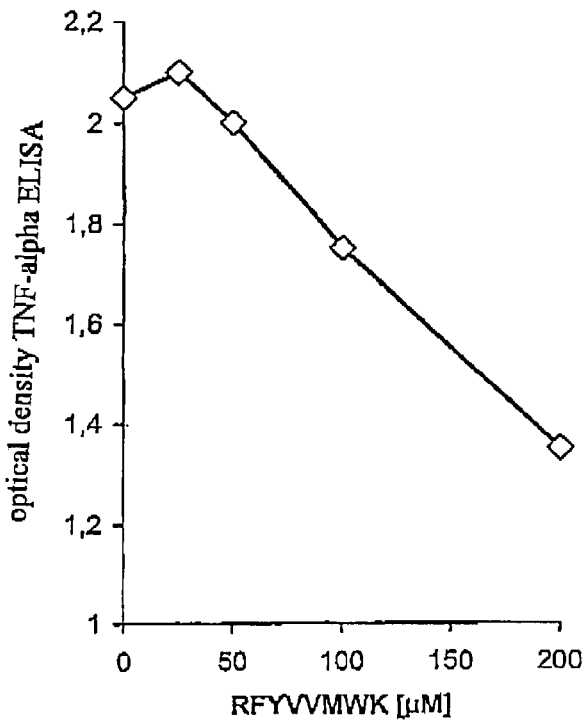
b)
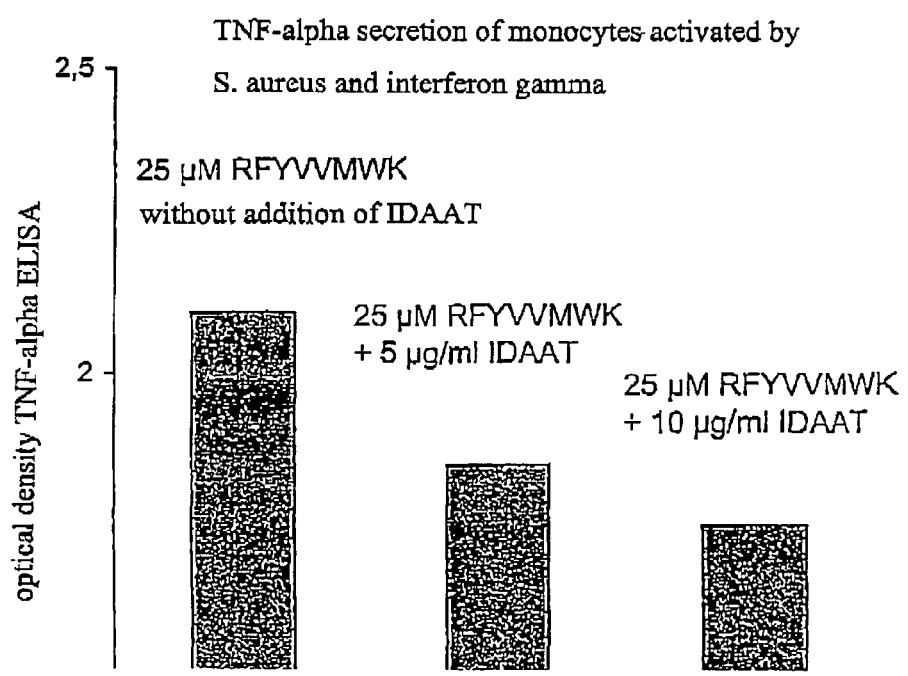

Fig. 11: IDAAT inhibits inflammatory reactions in vivo — Arthus reaction
a)
b)
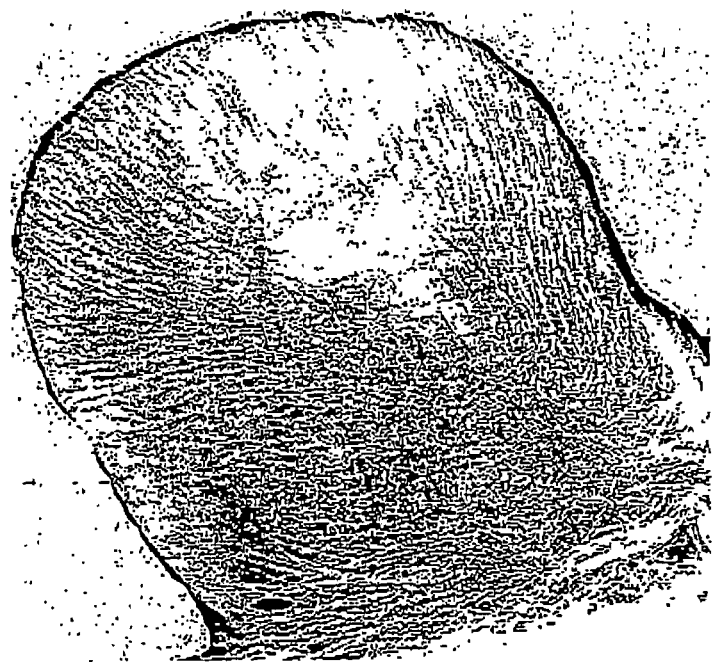

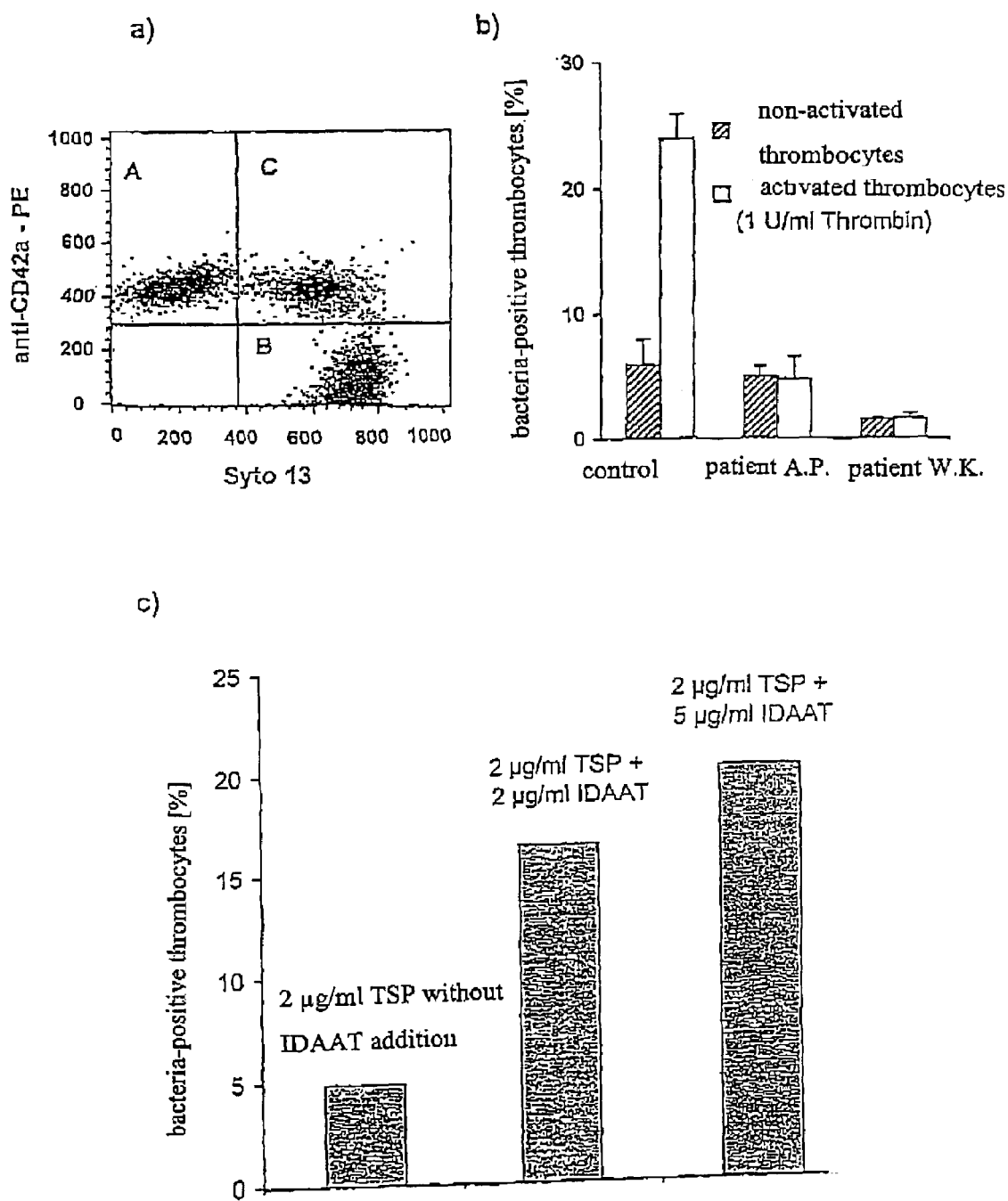
Fig. 12: IDAAT mediates S. aureus binding to cells capable of phagocytosis and bacterial defence

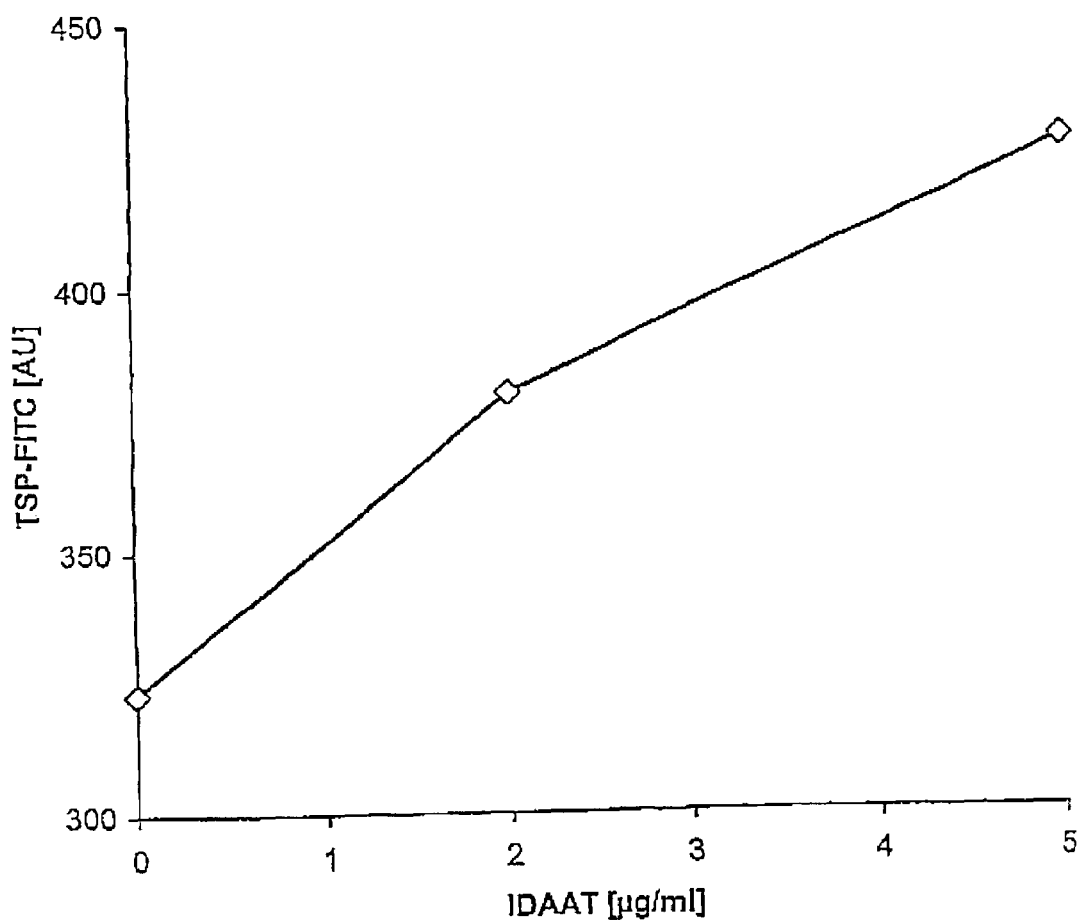
Fig. 13: IDAAT mediates the binding of thrombospondin to thrombocytes Fig. 14: IDAAT promotes the binding of fibrinogen to thrombocytes
a)
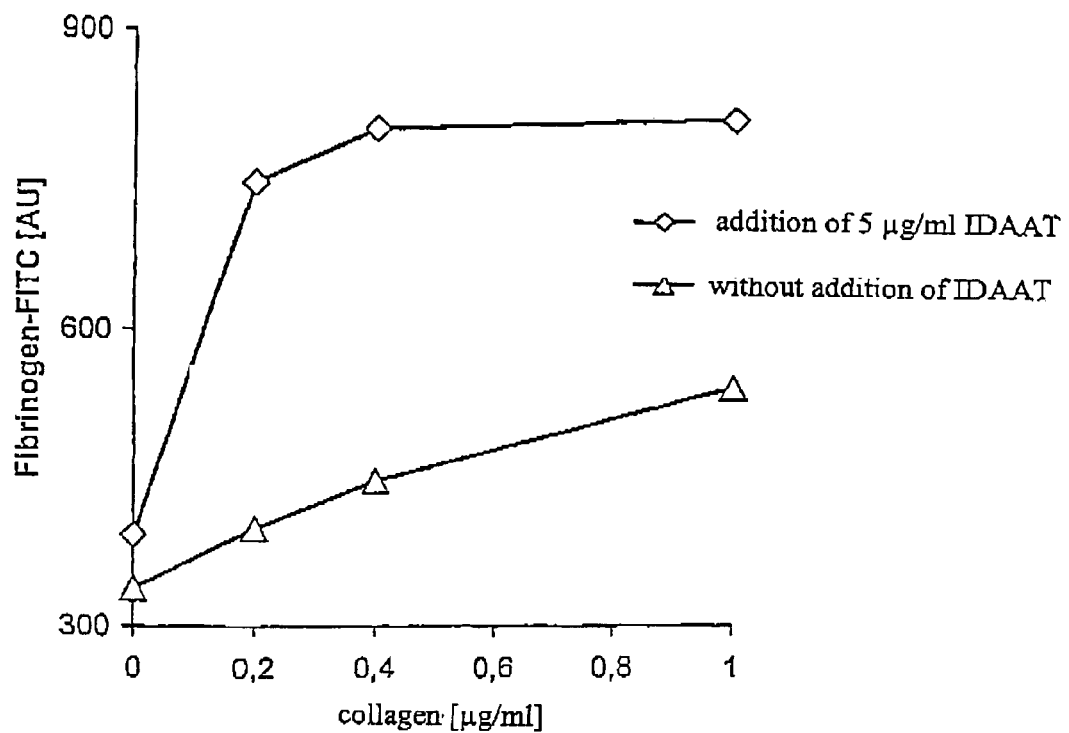
b)
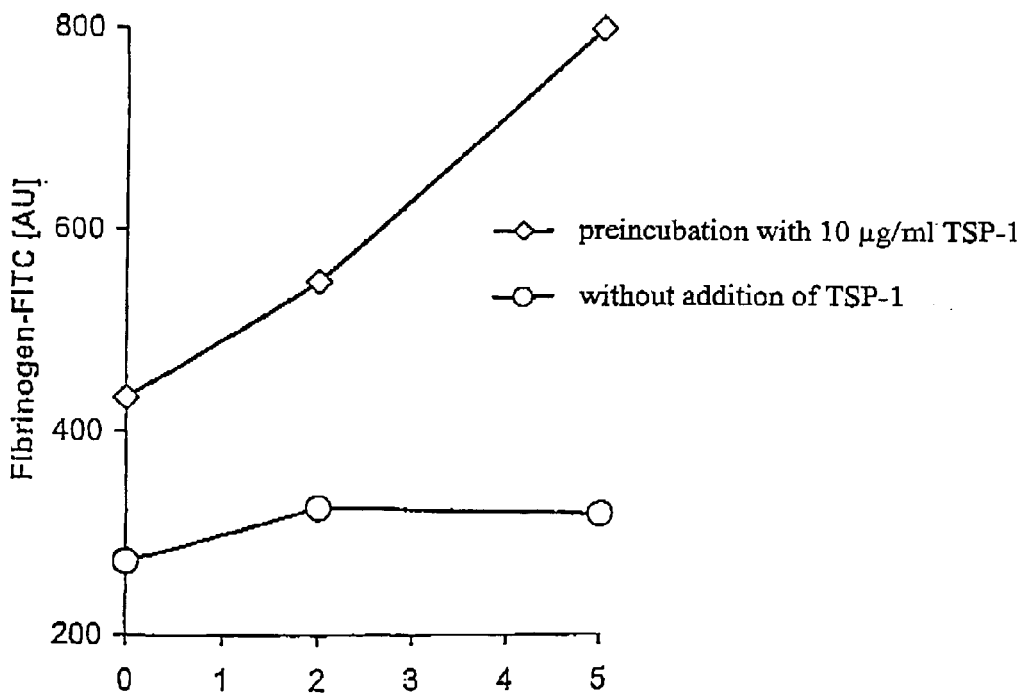

Fig. 15  IDAAT increases the adhesion of thrombocytes to adhesion proteins
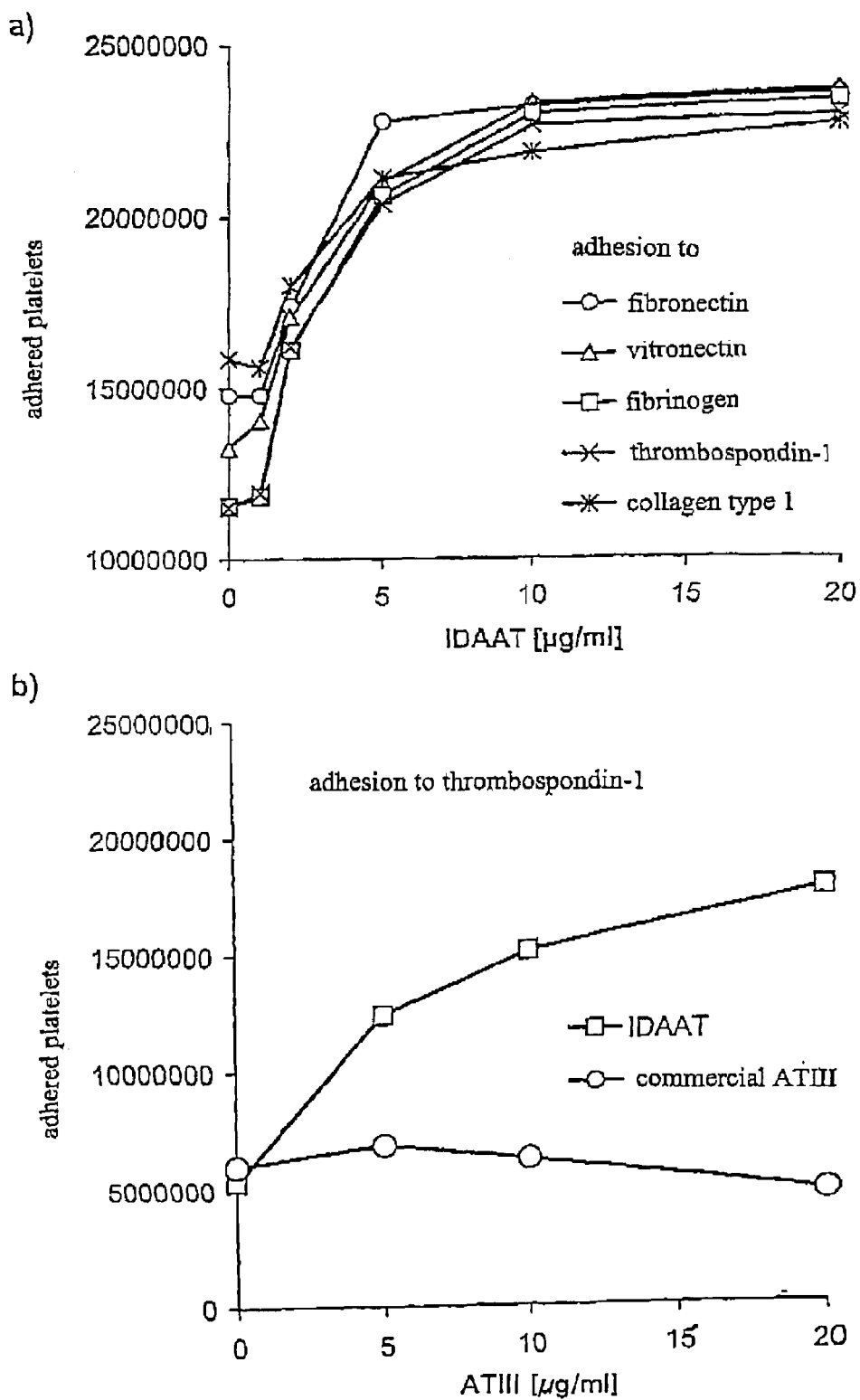

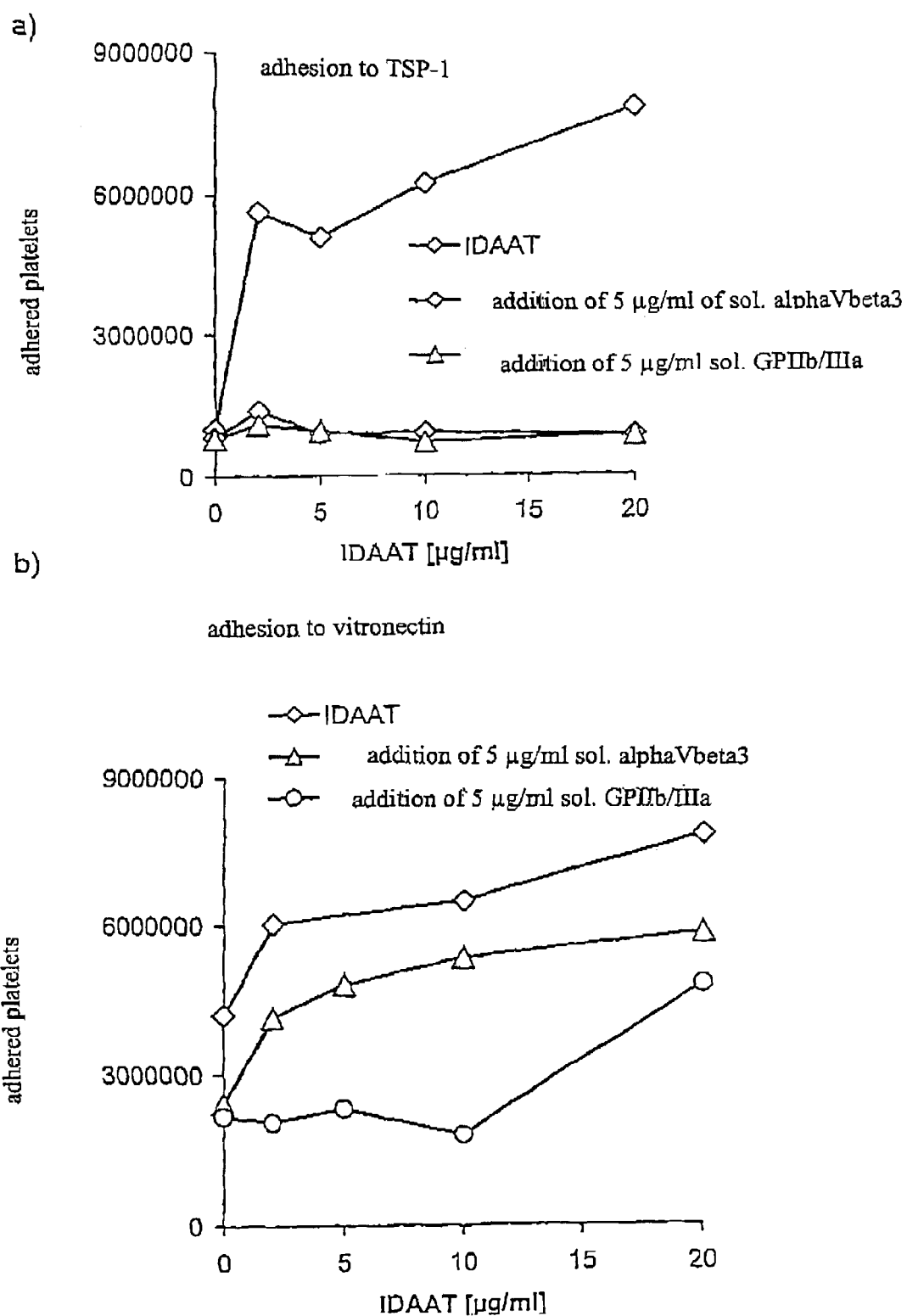
Fig. 16: IDAAT mediated adhesion of thrombocytes is integrin-dependent

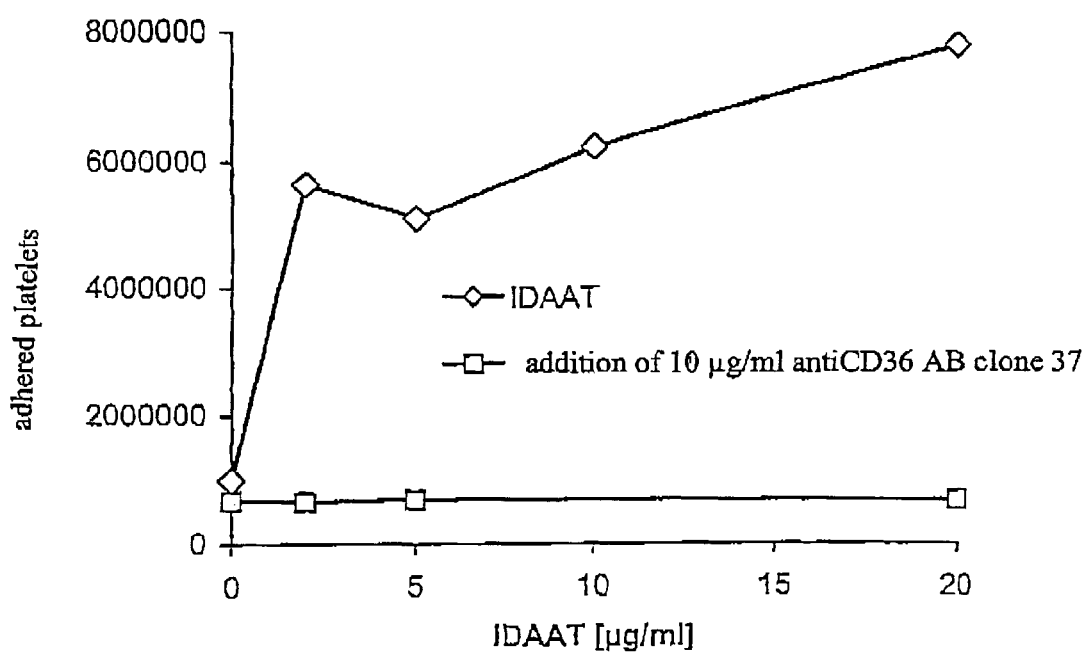
Fig. 17  Increase of thrombocyte adhesion by IDAAT is mediated by CD36

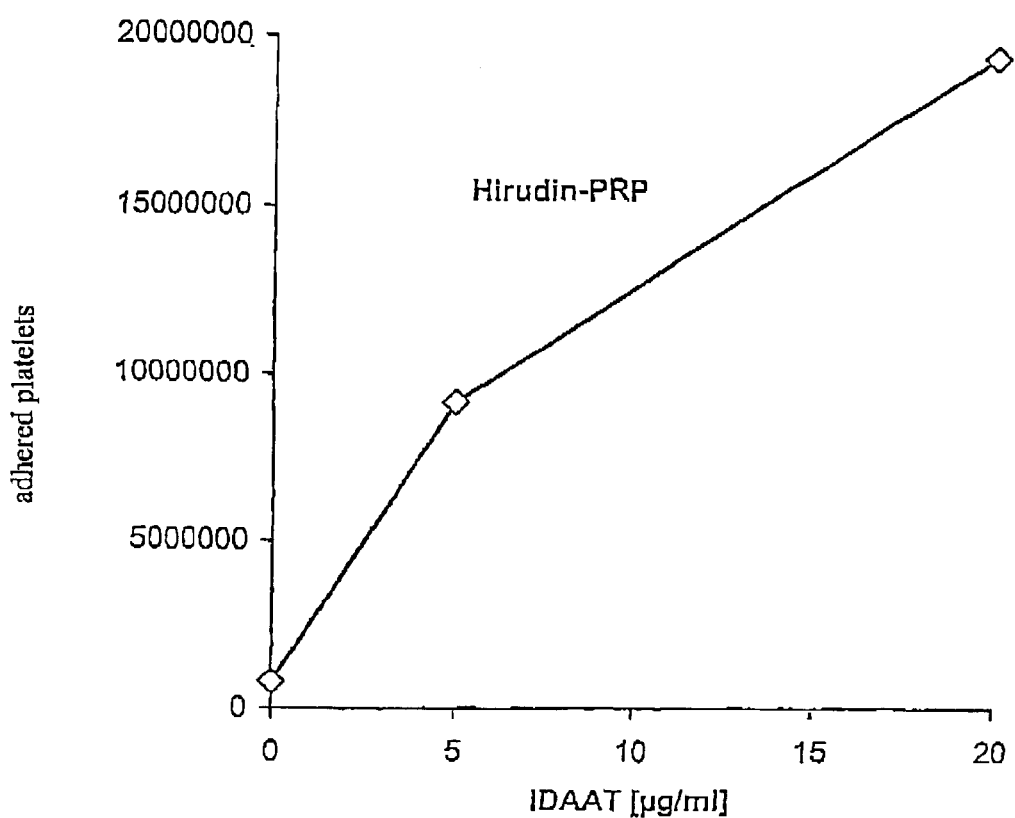
Fig. 18: Effect of IDAAT is independent of thrombin

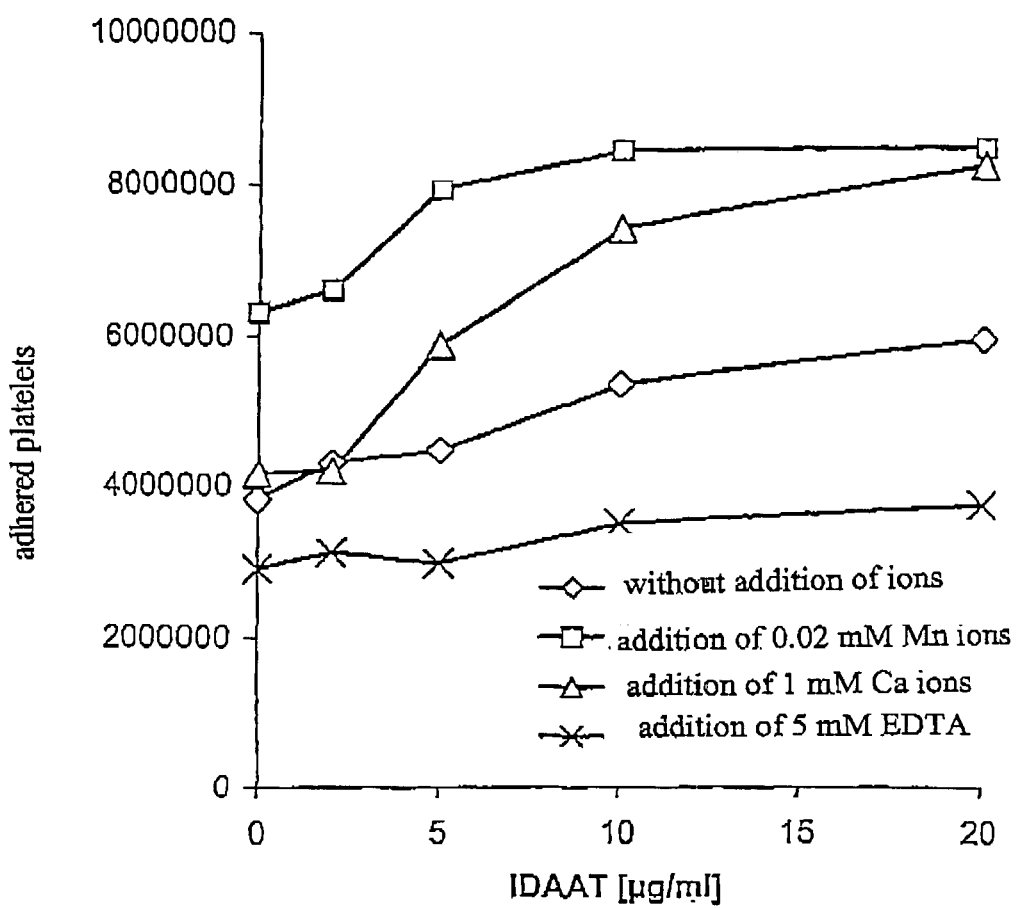
Fig. 19: IDAAT mediated adhesion of thrombocytes is dependent on divalent ions

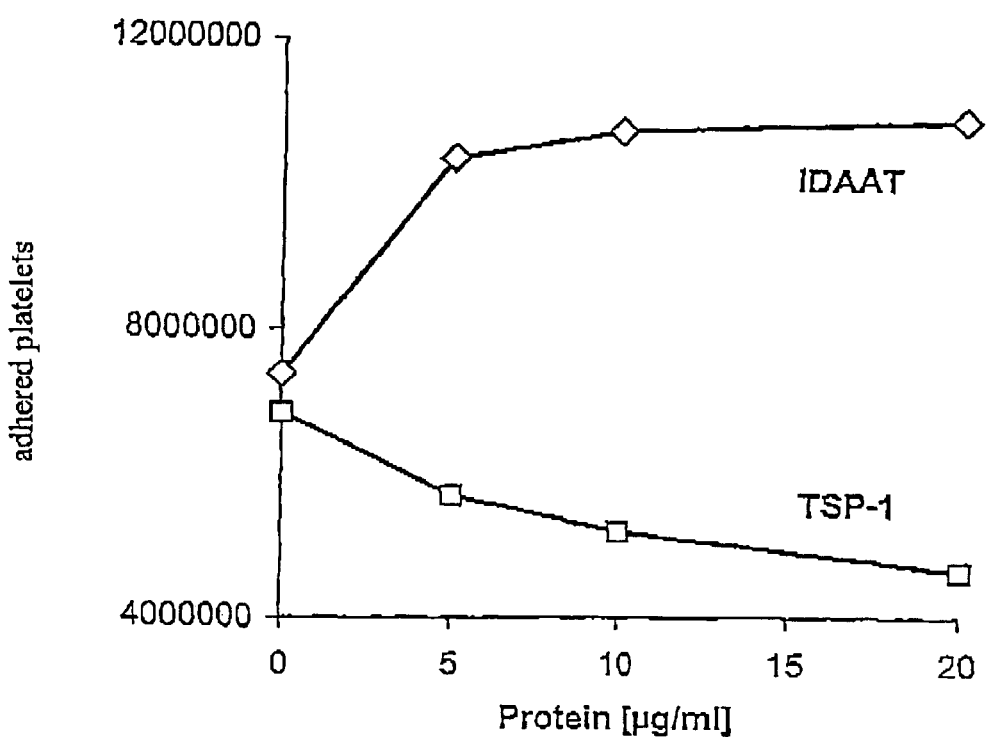
Fig. 20: Soluble thrombospondin-1 inhibits the adhesion of thrombocytes to collagen Fig. 21: Influence of blood cells on the IDAAT-mediated adhesion of thrombocytes
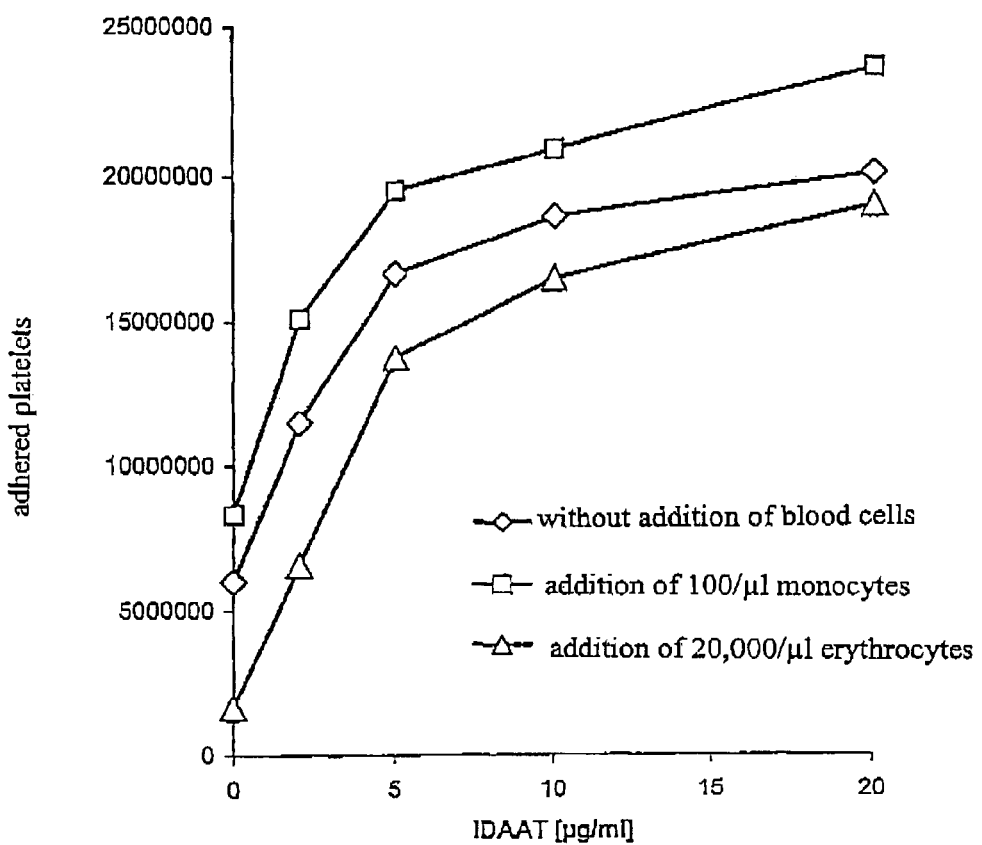

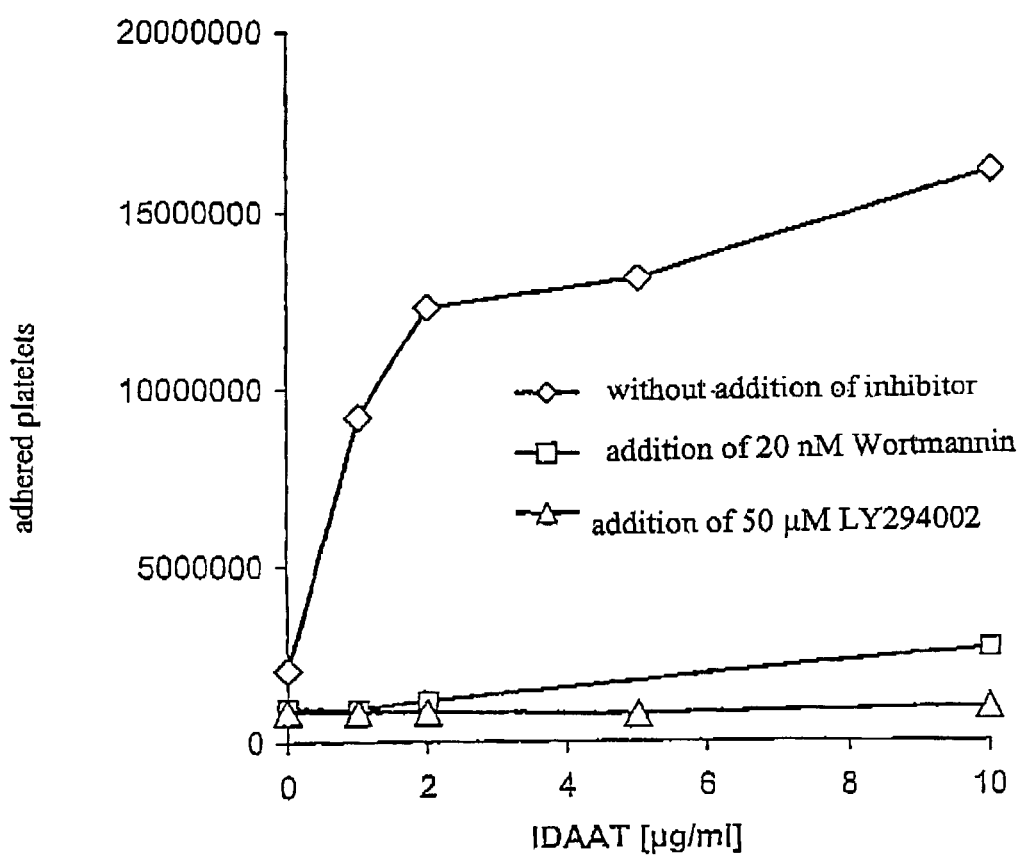
Fig. 22: IDAAT-induced thrombocyte adhesion is inhibited by inhibitors of PI-3 kinase

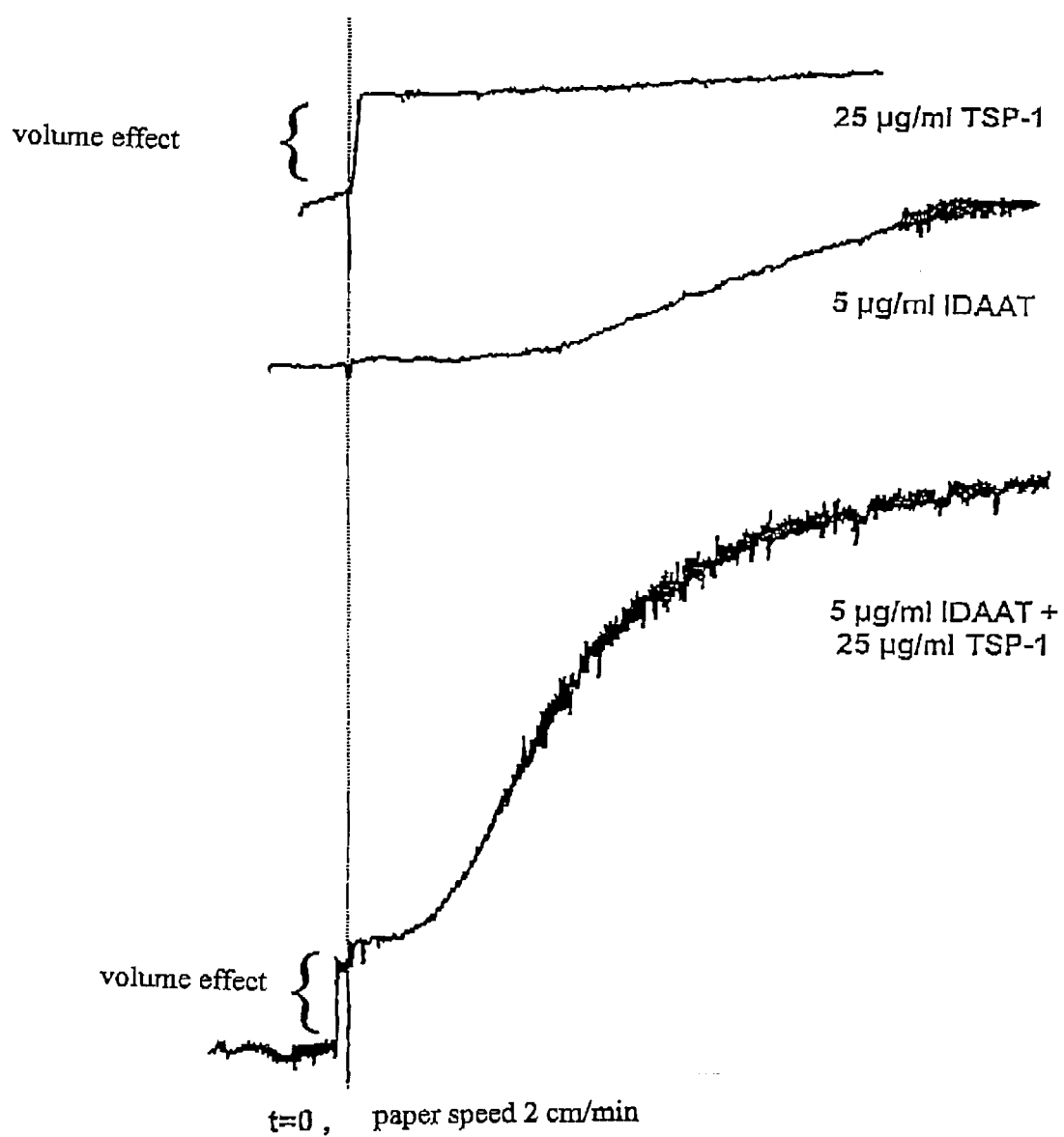
Fig. 23: IDAAT mediates thrombospondin-mediated thrombocyte aggregation

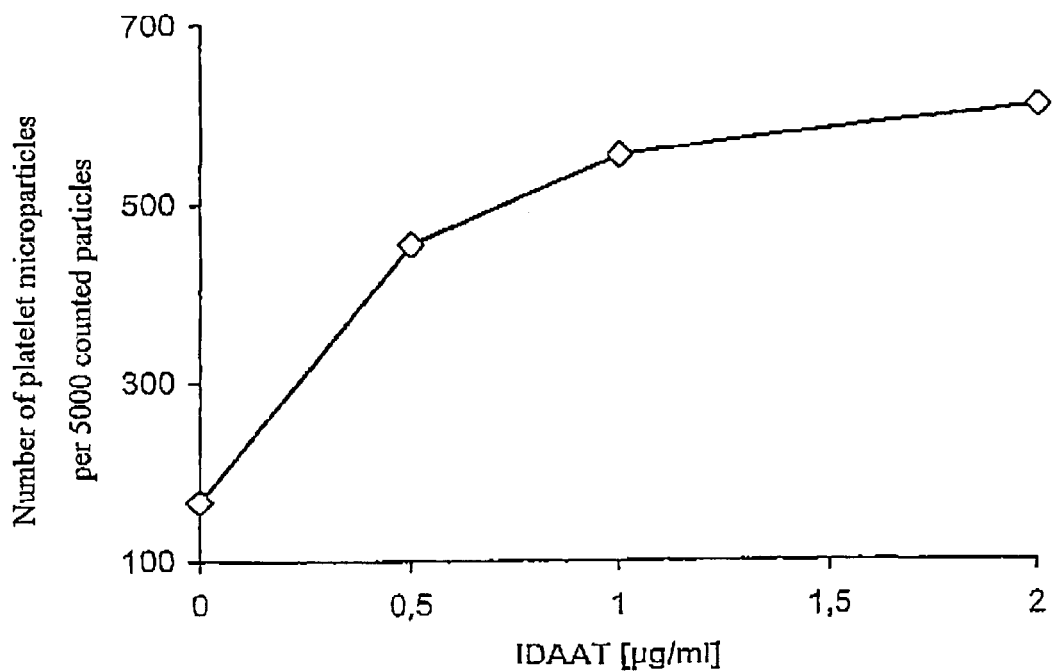
Fig. 24: IDAAT mediates the microparticle formation by thrombocytes

Fig. 25: IDAAT mediates the thrombospondin-1 binding to endothelial cells
a)
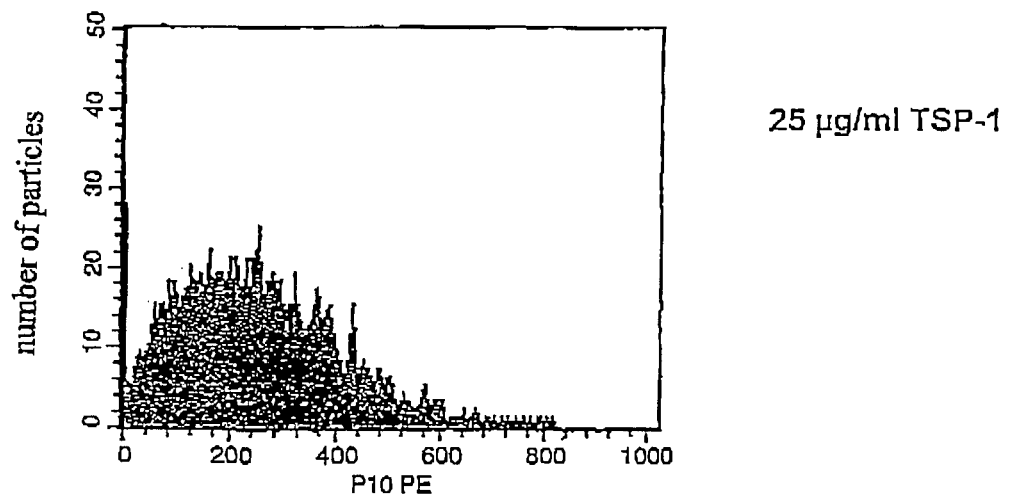
25 µg/ml TSP-1
b)
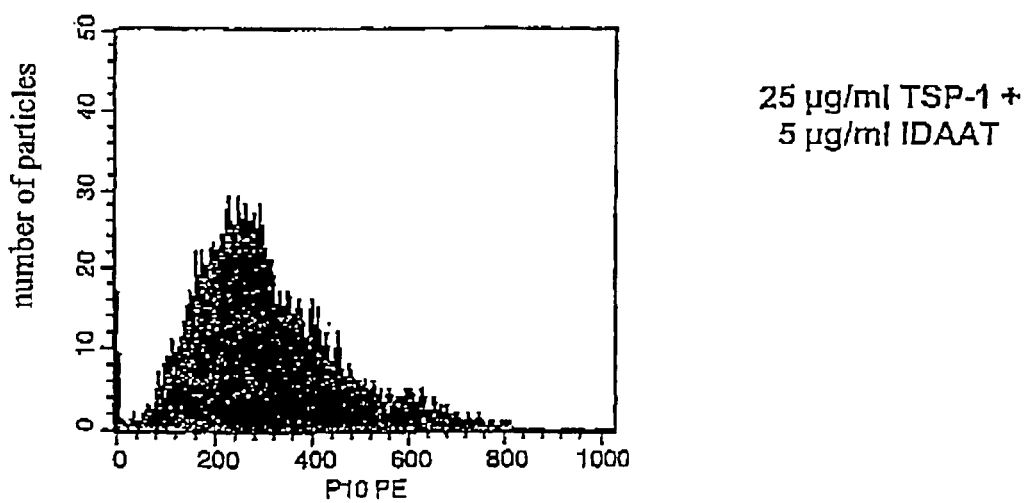
25 µg/ml TSP-1 + 5 µg/ml IDAAT

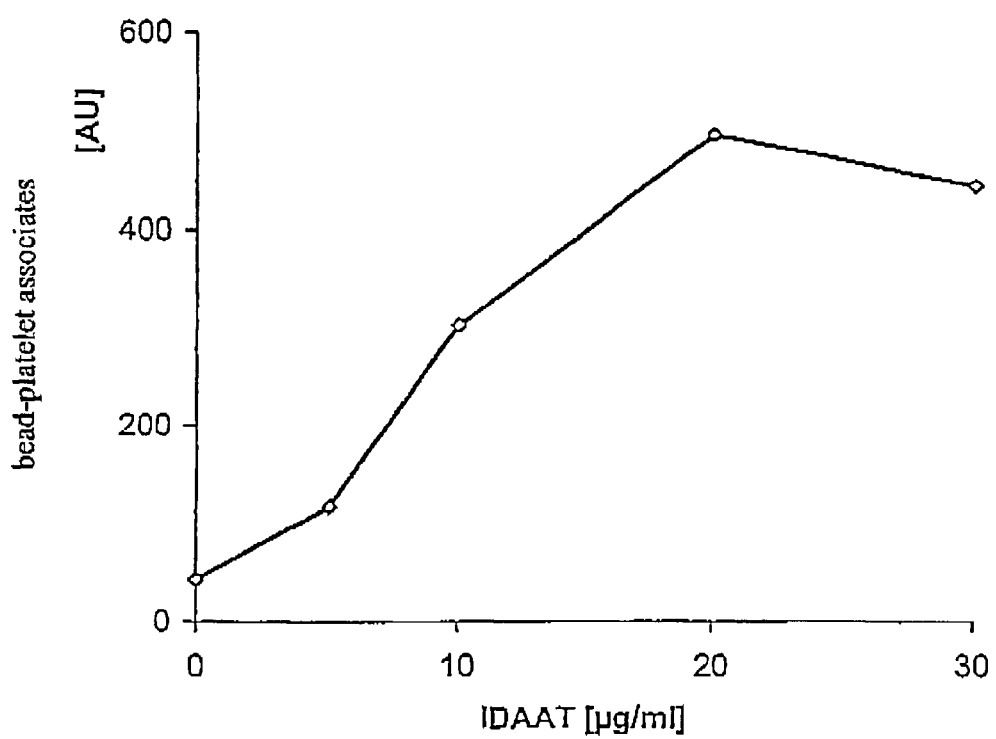
Fig. 26: IDAAT increases the binding of thrombocytes to vitronectin-coated latex beads Fig. 27: IDAAT is composed of polymerized antithrombin, IDAAT binds thrombospondin a) IDAAT b) commercial ATIII (K)

c) IDAAT binds TSP-1 d) commercial ATIII (K) does not bind TSP-1

Fig. 28: IDAAT binds to rec. CD4

Fig. 29: IDAAT binds to rec. HIV-GP 120
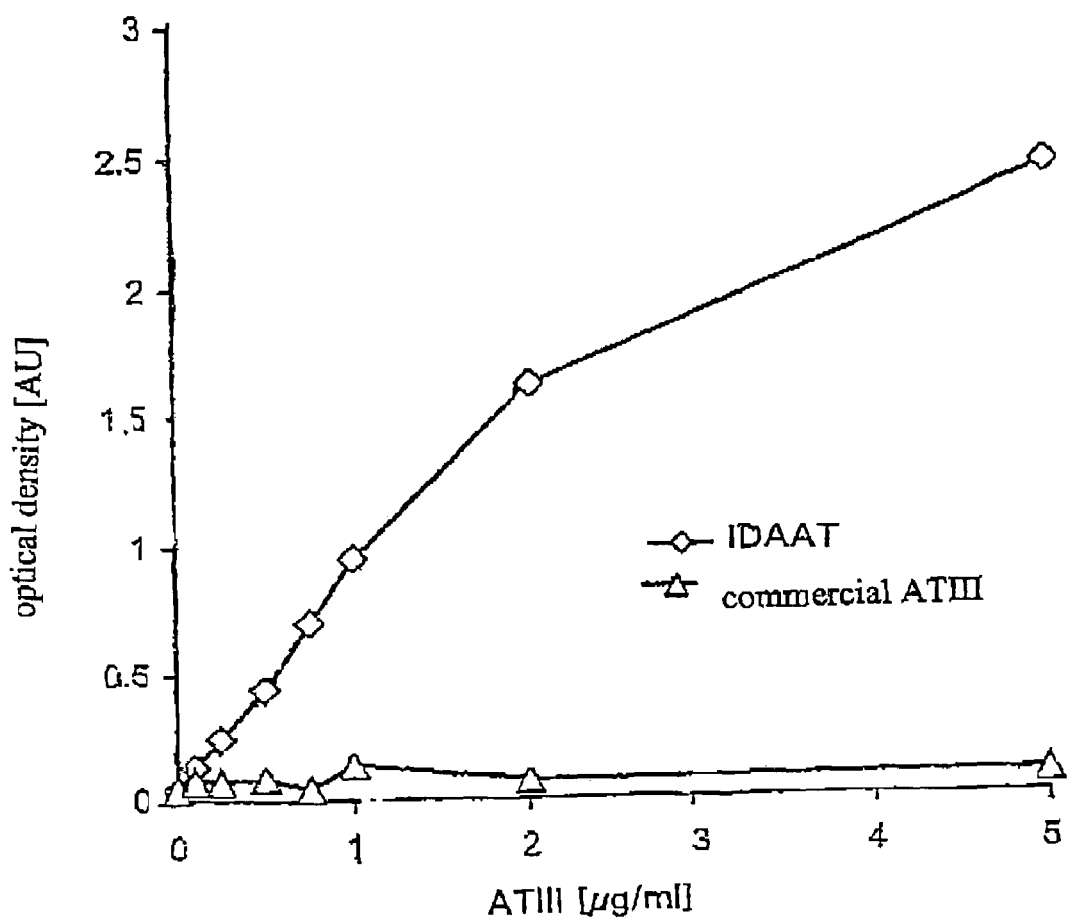

Fig. 30: IDAAT binds directly to thrombospondin
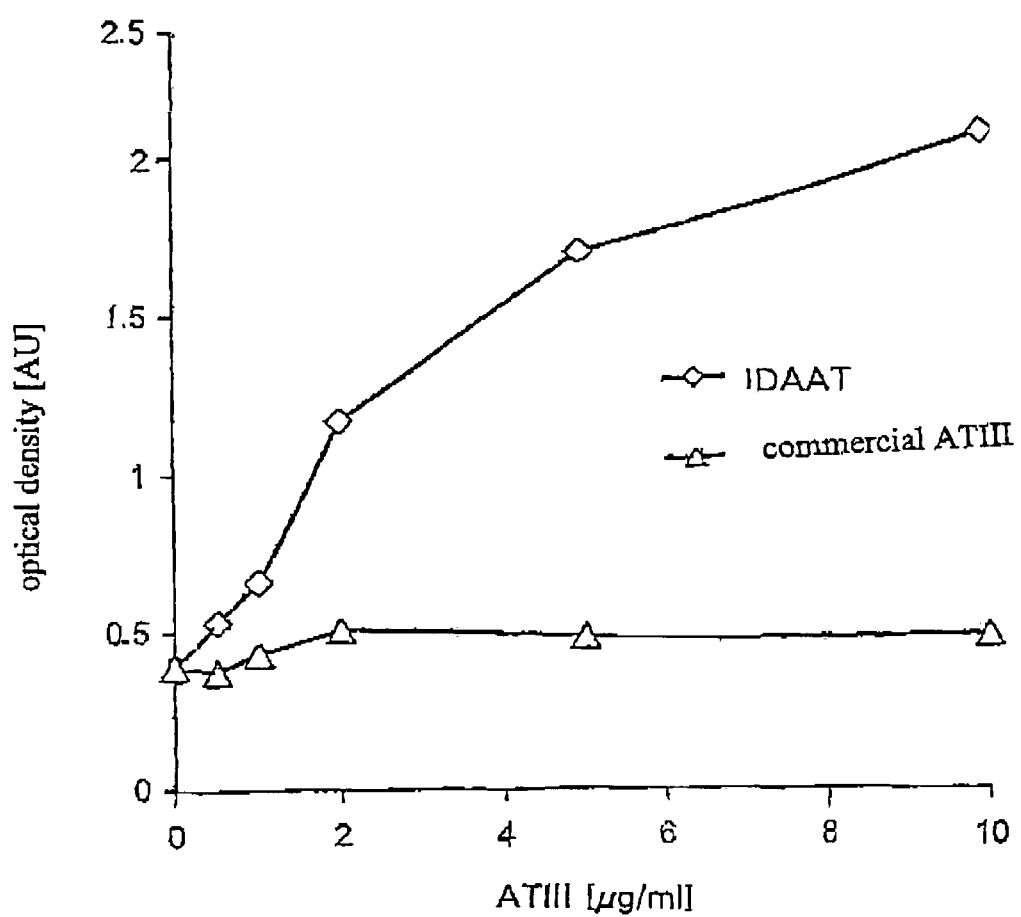

Fig. 31: IDAAT binds directly to vitronectin
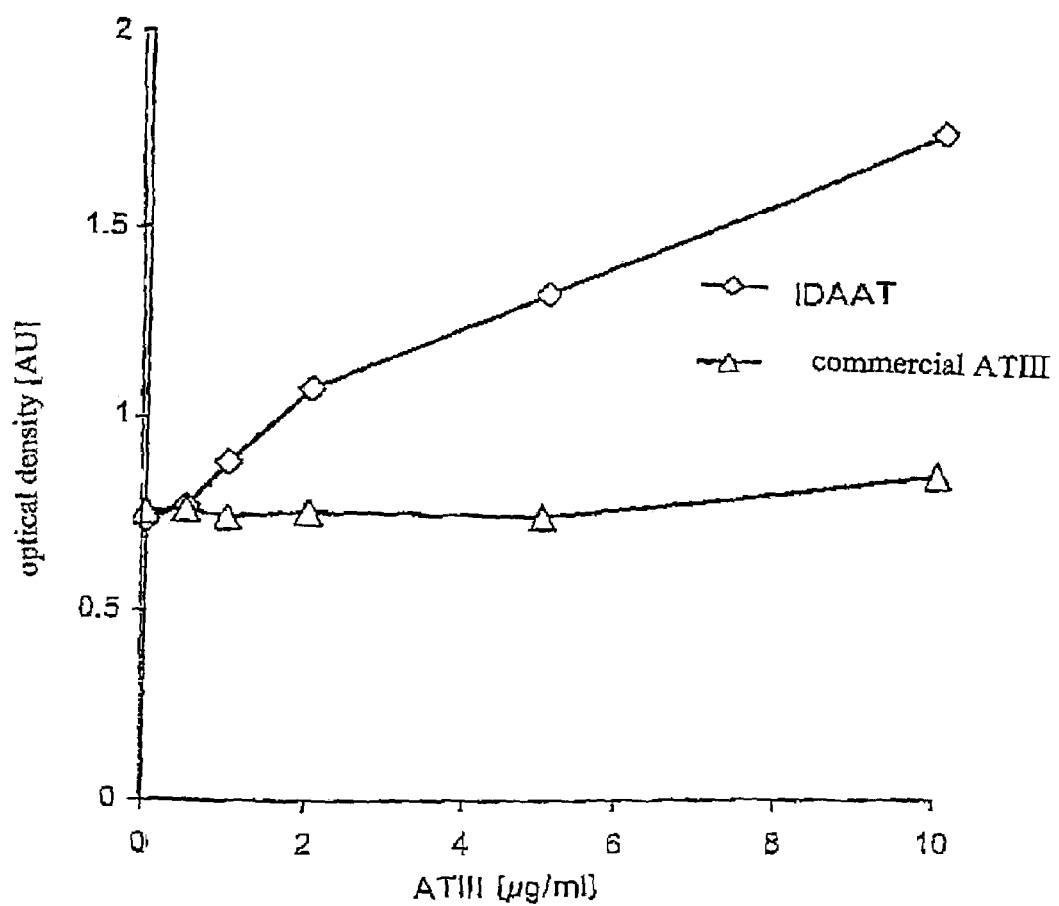

SEQUENCE LISTING

```
<160> NUMBER OF SEQ ID NOS: 2

<210> SEQ ID NO 1
<211> LENGTH: 6
<212> TYPE: PRT
<213> ORGANISM: Homo sapiens

<400> SEQUENCE: 1

Ser Glu Ala Ala Ala Ser
1               5

<210> SEQ ID NO 2
<211> LENGTH: 8
<212> TYPE: PRT
<213> ORGANISM: Homo sapiens

<400> SEQUENCE: 2

Arg Phe Tyr Val Val Met Trp Lys
1               5
```

MEDICAMENT CONTAINING ACTIVATED ANTITHROMBIN III

The invention concerns the use of antithrombin III with a modified conformation referred to here as activated antithrombin III (IDAAT=immune defence activated antithrombin) as a pharmaceutical preparation.

Antithrombin III is an important physiological coagulation inhibitor which inhibits circulating serine proteases without requiring a prior activation.

After forming a complex the protease cleaves the arginine 393-serine 394 bond which results in a conformation change of antithrombin and in protease-inhibitor complex formation. Heparin substantially accelerates the antithrombin-protease complex formation by binding in the amino-terminal region of antithrombin III. It is assumed that glycosoaminoglycans such as heparan sulfate assume the role of heparin on the surface of the endothelium.

Antithrombin III belongs to a family of serine protease inhibitors (serpins) which has over 100 members and it is a glycoprotein. Its polypeptide chain consisting of 432 amino acids has a molecular weight of 58000. The protein contains three intramolecular disulfide bridges and four glycosylation positions. When administered in extremely high unphysiological doses, antithrombin III reduces the mortality of sepsis in animal experiments (Dickneite and Paques, 1993). However, commercial antithrombin III preparations were not able to significantly improve the mortality or morbidity of humans suffering from sepsis.

In addition to the inhibitory effect on serine proteases and in particular on thrombin, antithrombin III was also observed to increase prostacyclin synthesis in human and bovine endothelial cells (Yamauchi et al., 1989). This increase led to a suppression of leucocytes (Kainoh et al., 1990) and is impaired by heparin (Uchiba et al., 1996) which led to the conclusion that this effect of antithrombin III is mediated by its binding to heparin-like glycosaminoglycan receptors. Moreover Stangl et al. 1999 described a slight increase (1.3- to 1.7-fold) in the release of endothelin-1 or big endothelin 1 from lung tissue of rats by antithrombin III.

The form of antithrombin III is changed by inflammation-mediated processes. The so-called "natural", "hereditary" or "constitutive" immune defence is the first defence strategy against "intruders" such as bacteria, viruses, parasites etc. and is widespread in the whole animal world. An important part of this first defence is that phagocytotic cells, in particular monocytes and PMNL (neutrophilic granulocytes) and also dendritic cells, eosinophils, blood platelets and mast cells, alone or in association with other cells migrate to the site of invasion of the pathogen (chemotaxis) and in this process penetrate through epithelia and endothelium (diapedesis).

At the site of inflammation the "foreign cells/intruders" are neutralized by phagocytosis. In this process the inflammatory cells release proteases such as elastase and cathepsin G and metalloproteases and substances which oxidize lipids, proteins and peptides.

These substances include $O_2$, superoxide, hydrogen peroxide, peroxynitrite, $OH^-$ radicals, hypochlorous acid HOCl, $Cl_2$ gas, chloramine. In this connection halogenation (mainly chlorination) is an important way of killing cells. In the inflamed region the pH value is decreased to below pH 4.0 by the release of lactic acid.

The defence cells also release specific proteins and peptides for defence such as bactericidal/permeability-increasing (BPI) protein from thrombocytes and granulocytes and defensins from granulocytes.

If there is a wound or other activation of hemostasis then thrombin, factor Xa and other serine proteases are formed in this process. In addition complement activation occurs (alternative path, properdin pathway) and there is an increased synthesis and release of so-called acute phase proteins such as fibrinogen, C-reactive protein, mannose-binding protein (MBP), products of so-called immediate early genes such as thrombospondin-1 and others. Activated mast cells release soluble heparin proteoglycan which can bind to antithrombin (Linstedt et al., 1992). Antithrombin III is indirectly or directly changed by these processes and acquires completely new functions.

Within the scope of the invention it was found that antithrombin III which is directly or indirectly changed by these processes acquires completely new functions.

It was also found within the scope of the present invention that antithrombin III can also be converted in vitro into this activated form especially by processes such as oxidation, treatment with urea and guanidine hydrochloride, proteolytic cleavage, heating to 60° C., lowering the pH to 4.0 or adding an ATIII peptide which contains the sequence SEAAAS (SEQ ID NO: 1). In this process a cryptic sequence of antithrombin is exposed and allows the protein to interact with proteins such as thrombospondin, vitronectin, CD36, oxLDL, $\alpha_V\beta_5$ integrin and others.

Furthermore it was found within the scope of the invention that activated antithrombin III (IDAAT) polymerizes by self association These polymers have repetitive binding sites for the adhering proteins and immobilize them. As a result the adhering proteins acquire functions which they do not have as soluble proteins in the plasma, serum or other body fluids and consequently they can stimulate signal transduction in membrane proteins. One of the most important interaction partners for IDAAT is thromobospondin-1 (TSP-1). TSP-1 is a modular glycoprotein composed of multiple domains which is released by many cells and is incorporated into the extracellular matrix. Blood platelets in particular contain high concentrations of TSP-1 (Flicker and Kehrel, 1993) in their α-granula and release it during their activation.

This results in a more than 1000-fold increase in the local TSP-1 concentration (Flicker and Kehrel, 1993). Endothelial cells, smooth muscle cells, glial cells and leucocytes secrete TSP-1. TSP-1 is a member of the thrombospondin family which also includes TSP-2, TSP-3, TSP-4 and the cartilage oligomeric matrix protein (COMP) (Lawler et al., 1993). Several regions of TSP-1 and TSP-2 are identical and thus several functions of TSP-1 can also be carried out by TSP-2. TSP-1 and TSP-2 have the same domain structure and can be expressed as homomers and heteromers (Bornstein et al., 1991). TSP-1 is a trimeric glycoprotein with an apparent mass of 420000 Da. Its 3 subunits have a molar mass of 180000 Da in the Lämmli SDS-PAGE system (Lawler and Hynes 1986). Electron micrographs show the trimeric structure which looks like a bola with globular ends at the amino and carboxy termini of the polypeptide chains (Galvin et al., 1985). The three chains are linked together by disulfide bridges near to the globular amino termini. Each TSP-1 subunit contains 69 cysteine residues so that each chain has at least one free SH group. TSP-1 and TSP-2 contain similar functional domains such as the N-terminal region, a pro-collagen homologous region, type 1 TSP repeats (repetitive regions), type 2 TSP repeats, type 3 calcium binding repeats and the carboxy terminal region (Bornstein et al., 1992).

The rod-shaped connecting regions of the TSP-1 chains exhibit a calcium-dependency of the structure. In the presence of $Ca^{2+}$ this structure has a length of 16 to 29.1 nm and in contrast a length of 38.3 nm after EDTA treatment (Lawler 1986).

The conformation of TSP-1 is strongly dependent on the $Ca^{2+}$ concentration (Lawler at al. 1988) and on the binding of interaction partners. Thus the binding of TSP-1 to fibronectin or heparin gives it a conformation in the absence of $Ca^{2+}$ which the molecule would adopt in the presence of $Ca^{2+}$ (Dardik and Lahav 1999).

Immobilized TSP adsorbed to surfaces mediates the adhesion of endothelial cells, smooth muscle cells and monocytes. This adhesion depends on the $Ca^{2+}$ conformation state of the TSP-1. EDTA treatment irreversibly inhibits this process (Lawler et al. 1988). The $Ca^{2+}$ form of TSP-1 enables it to bind to cells which is RGD-mediated via integrins. The binding of CD36 also changes the conformation of the TSP-1 molecule (Leung et al. 1992). TSP-1 binds to CD36 by means of a two-step mechanism. TSP-1 only binds with high affinity to CD36 in the second step by means of the cell binding site in the properdin-like type 1 repeat.

Binding to CD36 via the peptide sequence 139-155 of CD36 enables a conformation change in TSP-1 which allows high affinity binding to the sequence 93-110. This region contains the sequence of CD36 whose binding ability is regulated by phosphorylation/dephosphorylation (Thr 92) (Asch et al., 1993). Constitutively phosphorylated CD36 binds collagen, CD36 dephosphorylated by cell activation acquires the ability to bind thrombospondin. The conformation of TSP-1 regulates its functional capability.

In addition to its ability to bind to cells via integrins and to mediate cell adhesion, other properties are also regulated by the conformation of TSP such as the modulation of fibrinolysis, inhibition of elastase and cathepsin G, improvement of wound healing and promotion of the growth of neurites.

TSP-1 deficient mice develop extensive acute and chronic organized bacterial pneumonia with massive infiltration of neutrophils and macrophages between the first and fourth week of life. Diffuse alveolar hemorrhage was observed. At a later stage of the infection a thickening and curling of the epithelium of the airways occurs compared to control mice of the same inbred strain which have TSP-1 (Lawler et al. 1998).

These results illustrate the importance of TSP-1 for defence against infections. TSP-1 negative mice produce significantly fewer off-spring than control animals. TSP-1 knock outs exhibit a pronounced iordotic curvature of the spine. This shows the importance of TSP-1 for the development and stabilization of the skeleton. TSP-1 deficient animals had a highly significant higher number of leucocytes in particular monocytes and eosinophils in peripheral blood.

TSP-1 is a multifunctional protein. When immobilized on surfaces, it promotes the formation of plasmin (Silverstein et al. 1986) and at the same time the immobilization protects the plasmin from inactivation by the alpha2 plasmin inhibitor. The invention described here i.e. the use of IDAAT results in an immobilization of TSP-1 on cell surfaces. The urokinase plasminogen activator (uPA) and the signal chain uPA (scuPA) bind to immobilized TSP-1 and thereby remain proteolytically active. The binding to immobilized TSP protects uPA from inhibition by the plasminogen activator inhibitor type 1 (PAI-1) (Silverstein et al., 1990). When scuPA binds to its receptor (scuPAR) a binding site is exposed which enables the binding of cell-associated TSP-1 and vitronectin (Vn) (Higazi et al., 1996). Thus immobilized TSP-1 enables proteolytic processes to also occur in a microenvironment in which no fibrin is present.

Together with plasmin, immobilized TSP-1 activates the latent transforming growth factor beta 1 (TGF-β-1) on the macrophage surface (Yehualaeshet et al., 1999).

TSP-1 also activates TGF-β on the endothelial surface (Schultz-Cherry and Murphy-Ullrich, 1993, Schultz-Cherry et al., 1994). TGF-β inhibits the proliferation of endothelial cells and acts anti-angiogenetically. Inhibition of angiogenesis by TSP-1 has been described many times (Iruela-Arispe et al., 1999, Jiminez et al., 2000). Complex formation between TSP and FGF-β1 (basic fibroblast growth factor) is also involved in this function (Murphy-Ullrich, 1993). Absence of TGF-β leads to massive disorders in the defence against infections which can lead to death (Kulkarni et al., 1993, Shull et al., 1992). The TGF-β deficient animals additional exhibited a strong autoimmune reactivity (Letterio et al., 1996) due to its effect on MHC class II antigen expression (Geiser et al., 1993).

Since TSP-1 immobilized on cell surfaces can activate TGF-β, it would appear that TSP-1 is involved via TGF-β in the described processes of defence against infections and autoimmune reactivity (Crawford et al., 1998). Together with TGF-β, immobilized TSP-1 regulates the proliferation of natural killer cells (NK) cells (Pierson et al., 1996). The TSP-1 deficient animals also exhibit corresponding immune deficiencies although they are less pronounced. Since the activated antithrombin which is described for the first time in this invention and which binds TSP-1, can immobilize TSP on cell surfaces, it is apparent that IDAAT can indirectly influence the activation of TGF-β.

However, TSP-1 also modulates immunological defence-relevant processes by other mechanisms. Thus a large number of microorganisms such as coagulase-negative *staphyloccoci* (Li et al., 2000), *enterococci* and *Porphyromonas gingivalis fimbriae* (Nakamura et al., 1999) adhere to immobilized TSP-1.

Erythrocytes infected with the malaria tropica pathogen adhere to immobilized TSP-1 (Roberts et al., 1985) and to the TSP-1 receptor CD36.

The parasite itself has a membrane protein which contains TSP-1 homologous regions. This protein TRAP (thrombospondin-related-anonymous (adhesive) protein) which is transported in the erythrocyte membrane enables the parasite to mediate the adhesion of infected erythrocytes to the vessel wall (Wegelnik et al., 1999, Kappe et al., 1999).

Other pathogens such as *Cryptosporidium parvum* or *Eimeria tenella* have TSP or TSP-receptor homologous domains which they use for cell adhesion (Sulaiman et al., 1999).

The HIV-1 virus uses a CD36 (TSP receptor) domain in its surface protein GP 120 to enable the HIV virus to bind to TSP as well as to CD4 on the host cells (Crombie et al., 1998). Hence purified TSP-1 can inhibit HIV-1 infections (Crombie et al., 1998).

Several complement proteins, C9, C8 alpha and C8 beta have modules with a high degree of homology to one of the repeat modules of thrombospondin (Patthy, 1988). Antistasin, properdin and F-spondin also have other domains that are homologous to TSP. F-spondin is, like thrombospondin itself, a substance which effectively improves lesions of the nervous system (U.S. Pat. No. 5,750,502). TSP can mediate the phagocytosis of apoptotic PMNL by binding simultaneously to apoptotic neutrophilic granulocytes (PMNL) and to macrophages. The concurrent interaction of TSP with its receptors $α_vβ_3$ integrin, CD36 and CD47 is responsible for this process (Savill et al., 1992). The phagocytosis of apoptotic PMNL regulates inflammatory reactions and prevents an uncontrolled overreaction. In contrast to the phagocytosis of necrotic PMNL or PMNL that have been excessively degraded, TSP-1 mediated phagocytosis of apoptotic PMNL occurs without the release of proinflammatory mediators (Stern et al., 1996).

Thus a timely TSP-mediated phagocytosis prevents an inflammatory overreaction. In addition the production of proinflammatory cytokines is actively inhibited by macrophages which have taken up apoptotic PMNL (Fadok et al., 1998). The cross-linking of the TSP receptor CD47 on monocytes by TSP-1 is achieved by the invention described here and additionally results in an inhibition of the release of active interleukin 12 (IL-12) (Armant et al., 1999, Demeure et al., 2000). Interleukin 12 is an important mediator of sepsis (Steinhauser et al., 1999).

The immobilization of TSP-1 on apoptotic PAL and on monocytes is thus a good method for positively influencing persistent chronic inflammations with drugs. These diseases also include all those in which an uncontrolled inflammatory reaction represents a part of the disease itself such as various forms of reperfusion damage, rejection reactions in organ transplantations and rheumatoid diseases.

TSP not only mediates the phagocytosis of apoptotic neutrophilic granulocytes but also of senescent eosinophils (Stern et al., 1996). This shows that TSP immobilization on the cell surface which is achieved by the invention described here is also a method for pharmaceutical treating undesired proinflammatory responses in diseases that are mediated by eosinophils such as allergies, asthma, parasitic diseases, certain tumours and connective tissue diseases. This prevents the release of highly toxic substances from the eosinophils which would damage or destroy the tissue.

TSP binds chemokines such as RANTES and thus prevents the chemokine from binding to its receptor (Barnes et al., 1998). This is another way in which TSP modulates inflammatory reactions and immune defence.

A drug which influences the function of TSP by changing its conformation or promoting its immobilization on cell surfaces of immunocompetent cells, limits undesired immune responses in diseases such as, but not limited to, rheumatoid arthritis, good pasture syndrome, insulin-dependent diabetes, pemphigus, pemphigoid, primary biliary cirrhosis, colitis ulcera, lupus erythematosus, graft-versus host disease, sepsis.

Immobilization of TSP on cell surfaces leads to a cross-linking of its receptor CD47. This cross-linking of CD47 on chronic lymphatic leukemia cells (CLL cells) causes specifically the cell death of these tumour cells (Mateo et al., 1999).

A substance which results in the binding of TSP to leukemia cells would therefore be an effective drug for treating CLL which is a lethal disease against which there is still no specific effective drug.

Thrombospondin not only inhibits neoangiogenesis by means of its effect on TGF-β but also by means of immobilization and binding to and activation of CD36.

Treatment of tumours in mice with TSP-1 leads to the inhibition of neoangiogenesis and to the apoptosis of endothelial cells (Jiminez et al., 2000).

Inhibition of tumour angiogenesis is a good method for limiting the growth of tumours by drags (Roberts et al., 1996). Hence a substance which mediates the binding of TSP to endothelial cells in tumours acquires antiangiogenetic and thus anticarcinogenic properties.

Neoangiogenesis can also cause blindness e.g. due to diabetes mellitus (Kaplan et al., 1999, Shafiee et al., 2000), age-related macular degeneration or prematurity in infants. A substance which mediates the binding of TSP to endothelial cells could also be used as a drug to treat this neoangiogenesis.

After injury the concentration of TSP increases significantly in the tissue around the injured region. After a balloon catheterization TSP can for example be already detected 1 hour after injury on the surfaces of the cells (Watkins et al., 1990, Munjal et al., 1990). The TSP on the cell surface increases further in the following days and then also increasingly accumulates in the matrix.

As wound healing progresses TSP disappears again from the cell membranes of the injured tissue.

One of the functions of TSP in the wound is to improve wound healing (U.S. Pat. No. 5,155,038). A substance which immobilizes TSP-1 in the wound, should improve wound healing.

TSP in the wound is expressed by the tissue cells and is also released by blood platelets during their activation.

About 1% of the total platelet protein and about ¼ of the protein content of the platelet α-granula is thrombospondin-1 (Kehrel et al., 1996). Released thrombospondin stimulates collagen-induced platelet aggregation (Kehrel et al., 1988). TSP contains a sequence RFYVVMWK (SEQ ID NO: 2) at the C-terminus which activates platelets via CD47 (Chung et al., 1999 and 1997). However, soluble TSP alone does not trigger aggregation when added to the blood, a platelet suspension or platelet-rich plasma.

Whereas platelets in suspension can only bind TSP in its $Ca^{2+}$ form, platelets adhere to the high as well as the low $Ca^{2+}$ form of thrombospondin immobilized on the matrix.

Hence an object of the present invention was to provide a pharmaceutical preparation which can carry out the above-mentioned functions and can thus have the expected effects.

This object is achieved by a pharmaceutical preparation containing activated antithrombin III (IDAAT), IDAAT-peptides, IDAAT-analogues or IDAAT-mimetics.

As already described above, within the scope of the present invention is was found that activated IDAAT can trigger or mediate numerous reactions in the body which can be utilized to treat diseases on the basis of the new properties and functions discovered by the present invention. These functions and properties are further elucidated in the following as are the diseases and pathological conditions that can be treated by this means. In many cases IDAAT can also be used for prophylaxis.

Within the scope of the present invention the pharmaceutical preparation can contain the complete IDAAT which can for example be prepared according to the process described in the examples. Theoretically it is also possible to isolate IDAAT from the body that has been formed as a result of defence reactions Furthermore it would also be possible to use IDAAT peptides which mediate interaction with proteins such as thrombospondin, vitronectin, CD36, oxLDL, $α_{IIb}β3$-integrin, $α_Vβ3$-integrin and others. Such suitable peptides can easily be found by preliminary experiments in which for example their interaction with one of the above-mentioned proteins is tested.

Analogues of IDAAT are also suitable within the scope of the present invention when they likewise mediate an interaction with the said proteins. Finally it is also possible to use IDAAT-mimetics which can exhibit the same effects and interactions as IDAAT due to their structure or/and functional groups.

Within the scope of the present invention it is preferred to use recombinant IDAAT in which case a recombinantly produced antithrombin III is treated in a suitable manner in order to obtain activated antithrombin III (see examples and this description). Peptides and analogues of IDAAT are also preferably synthesized in a recombinant form and then activated.

A pharmaceutical preparation according to the invention can of course also contain other pharmaceutically acceptable auxiliary substances or/and excipients wherein the pharmaceutical preparation is formulated for local, intradermal, superficial, intraperitoneal, intravenous or intramascular or oral administration or it is administered by means of vesicles. Hence the pharmaceutical preparation according to the invention preferably contains those auxiliary substances and excipients which enable the respective preferred type of application.

The pharmaceutical preparation according to the invention can contain other substances apart from IDAAT or parts or analogues or mimetics thereof such as antibiotics, immunosuppressants etc. Depending on the disease to be treated it may be advantageous to support the treatment with known pharmaceutical preparations. Hence a corresponding combination of this pharmaceutical preparation with IDAAT or its analogues is optionally a preferred embodiment of the present invention.

Due to the processes in the body brought about by activated antithrombin III that have been found within the scope of the present invention, the pharmaceutical preparation according to the invention can be used for numerous indications. Examples of new functions of IDAAT are listed in the following that are not exhibited by antithrombin preparations and in particular by commercial antithrombin preparations:

1) IDAAT Mediates Specifically and Dose-dependently the Binding of TSP-1 to Monocytes, Monocytic Cell Lines and Monocytic Cells such as Macrophages.

Whereas without the addition of purified TSP-1 and without the addition of IDAAT only ~1% of eluted human monocytes could be detected in a flow cytometer by an antibody (clone P10) which recognizes TSP-1 on the cell surface, the number increases to ca. 5% by adding 10 μg/ml purified TSP-1.

The addition of IDAAT (without the addition of purified TSP-1) mediates the TSP-1 binding of endogenous TSP to monocytes. Ca. 18% of the monocytes were TSP-1 positive.

As a result of the simultaneous addition of TSP and IDAAT almost all (>90%) of the peripheral blood monocytes used were strongly positive for TSP (see FIG. 1).

2) IDAAT Mediates the Binding of TSP to Apoptotic PMNL

PMNL that were made apoptotic by aging (24 h incubation in cell culture medium in an incubator according to Savill, 1992) bind TSP. This process is dose-dependently and specifically increased by adding IDAAT (see FIG. 2). Simultaneous addition of purified TSP and IDAAT further increases the effect.

3) IDAAT Cross-links Apoptotic PMNL with Monocytes by Means of TSP

The addition of TSP and IDAAT leads to a dose-dependent association of apoptotic PMNL with monocytes (see FIG. 3).

4) IDAAT Stimulates Dose-dependently the Transmigration of Monocytes through Endothelium Transmigration experiments were carried out as described by Kielbassa et al., 1998. The addition of IDAAT to the culture medium of the monocytes during a transmigration experiment stimulates dose-dependently the transmigration of monocytes through the endothelium by 2-3-fold (see FIG. 4).

The addition of purified TSP (25 μg/ml) also stimulates the transmigration of monocytes. The addition of TSP and IDAAT leads to an increase in the transmigration at a low concentration of TSP and IDAAT which is larger than the transmigration caused by the addition of the individual substances alone.

5) IDAAT Activates Monocytes

IDAAT induces dose-dependently the $Ca^{2+}$ flux in monocytes. The $Ca^{2+}$ measurement was carried out according to Sorrani et al., 1993. Eluted monocytes ($5\times10^6$/ml) were washed at room temperature with Hepes-Tyrode buffer pH 7.4 and subsequently labelled for 15 minutes with 1 μM Fura2/AM at 37° C., washed twice in Hepes-Tyrode buffer without $Ca^{2+}$ and then taken up in Hepes-Tyrode containing 1 mM $Ca^{2+}$.

$Ca^{2+}$ signals induced by IDAAT, the TSP peptide RFYV-VMWK (SEQ ID NO: 2) and substances acting as positive or negative controls, were determined fluorimetrically in the Hitachi F-2000.

IDAAT (100 μg/ml) activates the monocytes and produces a substantial $Ca^{2+}$ signal (see FIG. 5).

6) IDAAT Mediates the Binding of TSP-1 to T Cells and to Dendritic Cells

IDAAT mediates the binding of TSP secreted by T cells and of exogenously added TSP to human T cells (in this case Jurkat cells as an example) (see FIG. 6).

7) IDAAT Dose-dependently Increases the Activating Effect of fMLF on the Oxidative Burst of PMNL The oxidative burst was induced essentially according to the instructions of the manufacturer using the Phago Test/Burst Test from the Orpegen Company (Heidelberg) on a flow cytometer, but the PMNL were firstly incubated with the substrate DHR123 and subsequently the PMNL were activated.

In this case IDAAT dose-dependently increases the activating effect of fLMF on the oxidative burst. IDAAT and fLMF both have an additive effect. IDAAT not only increases the activating effect of other agonists on the oxidative burst of PMNL, but also triggers it as an independent agonist (see FIG. 7). Hence IDAAT is a valuable tool for increasing the defence against infections.

8) IDAAT Specifically and Dose-dependently Inhibits the Release of Active Interleukin 12 (IL-12) by Activated Monocytes Active IL-12 plays a negative key role in inflammatory reactions and sepsis. Monocytes activated with interferon γ (INFγ) and *Staphylococcus aureus* produce and release IL-12.

This reaction was dose-dependently inhibited by IDAAT. The concentration of active IL-12 in the culture medium of the monocytes was determined by means of an ELISA.

The release of IL-12 was completely inhibited by incubating the monocytes with IDAAT (see FIG. 8).

In contrast to the secretion of IL-12, the secretion of IL-10 which has a protective effect in sepsis is dose-dependently increased by IDAAT (see FIG. 9). This illustrates the modulating effect of IDAAT in infective defence and suggests the utility of IDAAT in septic reactions. The release of another damaging interleukin, TNF α is inhibited by IDAAT (see FIG. 10).

9) IDAAT Inhibits Inflammatory Reactions in vivo

An Arthus reaction was produced in the ear of Balb-C mice by local injection of anti-BSA at the time 0 and simultaneous injection of FITC-coupled BSA into the peritoneum. In control animals (negative controls) only FITC (without BSA) was injected into the peritoneum. A very pronounced inflammatory reaction with swelling of the ear (oedema), FITC incorporation, infiltration of PMNL and petechial hemorrhaging into the tissue was observed after about 6 hours in the animals treated with anti-BSA and BSA-FITC.

50 μg IDAAT in buffer was additionally injected into the peritoneum of 8 mice at time 0 and after 0+3 hours.

6 control mice only received the buffer, 50 mM Tris/HCl buffer containing 150 mM NaCl pH 7.4 in which the IDAAT is usually dissolved instead of IDAAT at time 0 and 0+3 hours.

IDAAT almost completely prevented the Arthus reaction. Mice treated with IDAAT exhibited significantly less FITC incorporation, significantly less thickening of the ear and almost no petechia compared to animals treated with buffer (see FIG. 11).

10) IDAAT Inhibits the HIV-1 Infection of Monocytic Cells from Peripheral Blood (PBMC)

PHA-activated PBMC were incubated together with negative human serum 1:100 (negative control) with neutralized V3loop specific antibodies positive control), with IDAAT (150 μg/ml) and with a CCR5-tropic HIV-1 primary isolate (903) from a patient and the virus production was examined after 5 days by means of a p24 ELISA.

For this freshly PHA-activated PBMC were taken up in RPMI 1640 medium+20% FCS+100 U/ml IL-2 at a cell concentration of $2\times10^6$ cells/ml and 200,000 cells/well 100 μl were distributed on a 96-well flat bottom plate.

Substances to be tested for inhibition:

Positive control: neutralizing human anti-V3loop antibody 1:100, negative control: negative human serum 1:100 and verum: IDAAT (150 μg/ml), were added to the cells in RPMI medium and incubated for 30 minutes at 37° C./5% $CO_2$. Subsequently the HIV-1 virus was added to the preparations: in each case 10 μl/well of the HIV-1 primary isolate 903 supernatant (CCR5-trop) containing 20,000 $TCID_{50}$ (50% tissue culture infective dose)/ml≅1000 $TCID_{50}$/ml per well.

These preparations were incubated overnight at 37° C./5% $CO_2$. On the next day the cells were washed three times with RPMI 1640 and new culture medium was added. On the $5^{th}$ day after infection the p24 ELISA assays were carried out.

P24 ELISA:

The α-p24 antibody (11-G7 [Niedrig, Berlin] and D7320 [Biochrom] recognize the p24 protein of the primary isolate variant 903. Maxi-Sorb ELISA plates (Nunc) were coated overnight with these antibodies. The virus supernatant from the inhibition experiment was inactivated with 1% Triton X-100. The inactivated virus supernatant and the alkaline-phosphatase-conjugated detection antibody (BC1071-AP [Aalto]) were both transferred to the wells after washing the coated wells with PBS and incubated there for 5 hours at 37° C. The wells were again washed with PBS, the dissolved substrate for alkaline phosphatase p-nitrophenyl phosphate [Sigma] was added to the wells and the colour development was measured after 20 minutes at 405 nm in an ELISA photometer. The parallel values in the p24 ELISA varied by up to 0.02 optical density (OD) units around a common mean.

Whereas the OD 405 nm for the negative control (≅no inhibition) was 0.8, the neutralizing antibody (positive control) reduced the OD to 0.12. 150 μg/ml IDAAT reduced the OD to 0.10.

The addition of IDAAT effectively inhibited the HIV-1 infection of the PBMCs.

11) IDAAT Mediates the Binding of *S. aureus* to Cells Capable of Phagocytosis and Defence Against Bacteria (Blood Platelets, Monocytes, PMNL)

Thrombocytes were labelled with a thrombocyte-specific phycoerythrin-conjugated anti-GPIX antibody (clone Beb 1). Bacteria (various *S. aureus* strains) were adjusted with Tris-buffered saline solution (TBS) to a number of 250,000 microorganisms/μl and labelled with the RNA-dye Syto 13 [MoBiTec, Göttingen] at a concentration of 2 μM. Labelled bacteria and labelled thrombocytes were co-incubated for 10 minutes at a ratio of 10:1.

The cell population were analysed in a flow cytometer. Cells that were positive for both fluorochromes were classified as associates (see FIG. 12a). Thrombin stimulation and release of TSP from the α-granula of the platelets increased the percentage of platelets carrying bacteria by 2.5-fold relative to the total number of thrombocytes. This increase was not observed when using platelets from two patients with gray platelet syndrome whose platelets do not contain TSP (see FIG. 12b).

IDAAT dose-dependently stimulates binding of *S. aureus* to thrombocytes (see FIG. 12c).

Since thrombocytes have a so-called microbicidal protein which can destroy bacteria, this function of IDAAT must also be rated as a valuable contribution to the defence against infection.

12) IDAAT Improves Blood Coagulation a) IDAAT Mediates the Binding of Thrombospondin to Thrombocytes.

Purified TSP-1 was labelled with FITC and added at a concentration of 50 μg/ml to gel-filtered thrombocytes (50,000/μl) in Hepes-Tyrode buffer containing BSA. IDAAT was added at increasing concentrations and incubated for 60 minutes at room temperature together with the platelets. Bound TSP-FITC on the thrombocyte surface was quantified in a flow cytometer. IDAAT mediates the binding of thrombospondin to thrombocytes (see FIG. 13).

b) IDAAT Stimulates Fibrinogen Binding to Thrombocytes

FITC-conjugated fibrinogen (150 μg/ml) was added to gel-filtered platelets (50,000/μl) in Hepes-Tyrode BSA buffer or in PPACK anti-coagulated platelet-rich plasma (50,000/μl). Platelet suspensions were activated with meth. collagen type I as described in Kehrel et al., 1998. IDAAT was added at increasing concentrations to an aliquot of the samples After incubation for 30 minutes at room temperature the platelets were fixed, washed and the fibrinogen binding was quantitatively determined in a flow cytometer. IDAAT increases the fibrinogen binding to platelets induced by collagen activation (see FIG. 14a).

The addition of purified thrombospondin +IDAAT at increasing concentrations had a platelet-activating property and led to fibrinogen binding to the platelet membrane (see FIG. 14b).

c) IDAAT Stimulates the Adhesion of Thrombocytes to Adhesion Proteins such as Thrombospondin, Fibrinogen, Fibronectin, Vitronectin and Collagen The adhesion of thrombocytes was carried out according to Santoro et at., 1994. Microtitre plates (96 well) were coated overnight at 4° C. with adhesion proteins at a concentration of 25 μg/ml and the plates were blocked with BSA. 100 μl gel-filtered platelets or platelet-rich plasma anticoagulated with hirudin (300,000 Plt/μl) were incubated in the wells for 1 hour at room temperature in a moist chamber. Non-adhering thrombocytes were thoroughly washed out. The number of adhering platelets was determined by lysing the platelets with Triton X-100 and determining the lysosomal enzyme hexosaminidase.

In order to calibrate the adhesion assay a calibration series containing a known and increasing number of platelets was added to the microtitre plate and the absorbance of the reacted substrate p-nitrophenyl-N-acetyl-β D-glucosaminide was determined in relation to the number of platelets. IDAAT dose-dependently increased the adhesion of thrombocytes to the tested adhesion proteins (see FIG. 15a). Commercial ATIII preparations did not have this effect (see FIG. 15b).

The increase of thrombocyte adhesion by IDAAT is an integrin ($\alpha_V\beta_3$, αIIbβ3)- and CD36-mediated reaction (see FIGS. 16 and 17).

The IDAAT mediated thrombocyte adhesion is not mediated by thrombin and therefore also occurs in blood anticoagulated with hirudin (see FIG. 18).

Heparan sulfate (0-10 μg/ml) and sulfatide (0-20 μg/ml) do not inhibit the IDAAT-mediated adhesion.

The IDAAT mediated thrombocyte adhesion is dependent on divalent ions. 5 mM EDTA completely inhibits this adhesion to thrombospondin and to collagen (see FIG. 9). 20 μM $Mg^{2+}$, 1 mM $Ca^{2+}$ or other divalent ions increase the IDAAT-mediated thrombocyte adhesion to collagen.

Soluble TSP-1 inhibits the IDAAT-mediated adhesion of thrombocytes to collagen or immobilized TSP-1 (see FIG. 20).

The adhesion of the thrombocytes to thrombospondin and to collagen is increased by addition of monocytes to the thrombocytes, whereas the addition of erythrocytes inhibits the adhesion of thrombocytes to TSP and to collagen (see FIG. 21).

The IDAAT-mediated adhesion of thrombocytes to thrombospondin can be completely inhibited by the PI-3-kinase inhibitor Wortmannin and LY294002 (see FIG. 22).

d) IDAAT Mediates the TSP-mediated Aggregation of Thrombocytes.

Gel-filtered platelets (200,000/μl) in Hepes-Tyrode buffer pH 7.4 containing fibrinogen (100 μg/ml) were examined in an aggregometer according to Born. Whereas purified thrombospondin (25 μg/ml) alone produced no aggregation, the addition of IDAAT led to a dose-dependent aggregation which was considerably increased by the simultaneous addition of TSP and IDAAT (see FIG. 23).

e) IDAAT-mediates the Microparticle Formation of Thrombocytes

Gel-filtered platelets were activated with the TSP-1 peptide RFYVVMWK (SEQ ID NO: 2) (40 μM). The microparticle formation was measured in a flow cytometer after labelling with a thrombocyte-specific anti-GPIX phycoerythrin conjugated antibody according to Dörmann et al. 1999. Addition of IDAAT led to a dose-dependent microparticle formation of the activated platelets (see FIG. 24).

f) IDAAT Mediates the Association of Thrombocytes and Leucocytes

In order to detect the platelet-leucocyte associates by means of flow cytometry the thrombocytes were labelled with a FITC-conjugated monoclonal antibody against the platelet-specific antigen GPIX (clone Beb 1) and the monocytes were labelled with a PE-conjugated monoclonal antibody against CD14 (clone: MΦP9) at saturating concentrations after cell activation and cell fixation. The associates were quantified by detecting CD14- and GPIX-positive particles. The percentage of leucocytes that were present associated with platelets was expressed as a ratio to the total leucocyte population Thrombocytes (25,000/μl) and monocytes (3000/μl) were incubated together for 30 minutes. The thrombocytes were previously pre-incubated for 30 minutes with IDAAT and subsequently washed. IDAAT increased the association rate from 11.7% to 17.3% (5 μg/ml IDAAT) and 20.5% (10 mg/ml IDAAT).

13) IDAAT Mediates/increases the TSP Binding to Endothelial Cells

Human microvascular endothelial cells (HMEC-1) (3000/μl) in RPMI 1640 medium were incubated for 30 minutes at room temperature with IDAAT or TSP-1 (25 μg/ml) plus IDAAT. The endothelial cells were fixed, washed and TSP was detected in a flow cytometer using a monoclonal PE-conjugated anti-TSP antibody (clone P10). The median of the fluorescence which is a measure for the binding of the anti-TSP antibody increased from 79 (without IDAAT) to 138 (5 μg/ml IDAAT). Addition of exogenous TSP-1 (25 μg/ml) increased the median fluorescence to 268 when IDAAT was also added (5 μg/ml) (see FIGS. 25a) and 25b))

14) IDAAT Mediates the Binding of Thrombocytes to Latex Beads Coated with Vitronectin Latex beads (3.2 μm) were coated overnight at 4° C. with active vitronectin (25 μg/ml) and then washed. Vitronectin-coated beads were incubated for 1 hour at room temperature with gel-filtered thrombocytes (25,000/μl) in the absence and presence of increasing concentrations of IDAAT.

Thrombocytes were labelled with anti-GPIX (clone Beb 1) and associates of vitronectin-coated beads with thrombocytes were quantified in a flow cytometer IDAAT dose-dependently increased the binding of thrombocytes to vitronectin-coated beads (see FIG. 26).

15) IDAAT is Composed of Polymerized ATIII

IDAAT, IDAAT-TSP-1 aggregates, commercial ATIII and commercial ATIII supplemented with TSP-1 were displayed in an electron microscope by means of the rotary shadowing method according to Jander et al. (1984). IDAAT consists of polymeric ATIII molecules whereas commercial ATIII preparations have a monomeric structure (see FIGS. 27a and b). The addition of TSP-1 to IDAAT led to die formation of large IDAAT-TSP-1 complexes, whereas this was not observed with commercial ATIII (see FIGS. 27c and d).

16) IDAAT has New Protein-binding Properties

IDAAT binds directly to proteins to which non-activated antithrombin cannot bind such as CD4 (e.g. T cells) (FIG. 28), GP120 of the HI virus (FIG. 29), thrombospondin (FIG. 30), activated vitronectin (FIG. 31), CD36, $\alpha_V\beta_3$ integrin. The binding of IDAAT to these proteins was carried out by means of an ELISA using purified or recombinant proteins. The purification of TSP-1, active vitronectin, $\alpha_{IIb}\beta_3$ integrin and CD36 was carried out as described by Kehrel et al., 1993, Yatohgo et al. 1988 and Kronenberg, Grahl and Kehrel 1998.

IDAAT Can for Example be Prepared within the Scope of the Present Invention as Follows:

Commercial antithrombin III is oxidized with NaOCl and applied to a Sephadex column (example 1). Antithrombin III can preferably be incubated with neutrophilic granulocyte elastase before oxidation (see example 2). Before the oxidation antithrombin III can also be cleaved with matrix metalloproteinase (see example 3). Antithrombin III can also be activated by reaction with defensin 2 (see example 4).

This process for preparing IDAAT is another subject matter of the present invention.

A further subject matter of the present invention is the use of a pharmaceutical preparation according to the invention, wherein the diseases or pathological states mentioned in the following can be treated in humans or animals. The pharmaceutical preparation according to the invention can be used for prophylaxis and as a curative agent. The indications are acute infections, especially infections with pathogens that directly or indirectly bind to IDAAT or an interaction partner and in particular the group of HI viruses, parasites such as *Plasmodium falciparum* and *Pneumocystis carinii* and bacteria such as *Staphylococcus aureus*; improvement of the immune defence and as an agent for the prophylaxis of sepsis in patients with a high risk of infection i.e. after operations with a high risk of infection, polytrauma, burns, intoxication, patients undergoing chemotherapy, immunosuppressed patients and patients with a predisposition for immune deficiency; or to therapeutically influence acute, chronic or allergic inflammatory reactions in particular to modulate inflammatory reactions in which the aim is to neutralize the damaging effects of apoptotic PMNL and eosinophilic granulocytes; as a curative agent for treating tumour growth and metastases; as an inhibitor of angiogenesis to combat undesired neoangiogenesis e.g. in tumours or patients with retinopathy; as a curative agent for leukemia in particular chronic lymphatic leukemia; to improve wound healing in particular for poorly healing wounds and in plastic surgery; to treat lesions in the nervous system in particular in diseases in which a growth of neurites is desired; to improve blood coagulation especially in patients with congenital or acquired thrombocytopathies, under anticoagulation therapy or in operations using a heart-lung machine; to prevent tissue damage due to inflammation e.g. in the case of a) reperfusions (e.g. stroke, myocardial infarction, ligations)

b) organ transplantations (prevention of transplant rejection) and c) allergic reactions (including neurodermitis, bronchial asthma).

When the pharmaceutical preparation according to the invention is used for the prophylaxis of diseases it can be applied alone or in combination with interaction partners or other medicaments or as au additive in rinsing fluids e.g. for the mouth, vagina, anus and eyes, as an additive to prevent the transmission of infections by sexual contacts (e.g. for condoms, diaphragms etc.) and in solutions, plasters and wound pads for wound care.

The pharmaceutical preparation according to the invention can be used locally, intradermally, superficially, intraperitoneally, intravenously, intramuscularly, orally or by means of vesicles in one of the above-mentioned forms of administration. Other possible forms of administration are also encompassed by the present invention.

The present invention is further elucidated by the following figures and descriptions thereof:

FIG. 1: IDAAT mediates the TSP-1 binding to monocytes

TSP-1-positive monocytes were labelled with the monoclonal anti-TSP antibody clone P10 which was conjugated with phycoerythrin and the fluorescence of the monocytes was measured in a flow cytometer.
  a) 3000 measured monocytes: monocytes were incubated for 30 minutes with Hepes-Tyrode buffer pH 7.4, washed and labelled with P10-PE
  b) 3000 measured monocytes; monocytes were incubated for 30 min at room temperature with TSP-1 (10 μg/ml) in Hepes-Tyrode buffer pH 7.4, washed and labelled with P10-PE
  c) 3000 measured monocytes: monocytes were incubated for 30 min at room temperature with TSP-1 (10 μg/ml) and IDAAT (10 μg/ml) in Hepes-Tyrode buffer pH 7.4, washed and labelled with P10-PE
  d) monocytes with and without addition of TSP-1 (10 μg/ml) were incubated with increasing concentrations of IDAAT (see above); IDAAT mediates the binding of TSP-1 that is added exogenously or which is present endogenously.

FIG. 2: IDAAT mediates the binding of TSP-1 to apoptotic polymorphonuclear granulocytes (PMNL)
  a) PMNL were made apoptotic by incubation in a cell culture medium for 24 hours in an incubator according to Savill et al., 1992. Apoptotic PMNL were incubated for 30 minutes with Hepes-Tyrode buffer pH 7.4, washed, labelled with the anti-TSP antibody P10-PE and the fluorescence of 3000 cells was measured in a flow cytometer
  b) PMNL were made apoptotic by incubation in a cell culture medium for 24 hours in an incubator according to Savill et al., 1992. Apoptotic PMNL were incubated for 30 minutes with TSP-1 (5 μg/ml) and IDAAT (10 μg/ml) in Hepes-Tyrode buffer pH 7.4, washed, labelled with the TSP antibody P10-PE and the fluorescence of 3000 cells was measured in a flow cytometer.
  c) Procedure as in a and b: IDAAT was used at increasing concentrations. IDAAT mediates the binding of thrombospondin (10 μg/ml) that was either present endogenously or added exogenously.

FIG. 3: IDAAT cross-links apoptotic PMNL with monocytes by means of TSP Eluted PMNL and eluted monocytes were incubated together for 30 minutes at room temperature with TSP and IDAAT at various concentrations and the cells were fixed. The PMNL were labelled with a monoclonal FITC-conjugated antibody against CD16b and the monocytes were labelled with anti-CD14-PE. PE and FITC positive associates were measured using a flow cytometer.

FIG. 4: A Transwell insert covered with a microporous polycarbonate membrane was placed in each well of the 24-wells in Transwell cell culture chambers (Costar, Bodenheim). The polycarbonate membrane which had a pore size of 5 μm was coated with fibronectin and human microvascular endothelial cells (HMEC-1) were cultured thereon until confluence.

Human monocytes isolated by density gradient centrifugation (200 μl containing $2 \times 10^7$ cells/ml in DMEM from peripheral blood) were added after one day of culture in the upper Transwell insert and incubated for 4 hours at 37° C., 7% $CO_2$ with the HMEC-1 monolayer. The number of monocytes in the lower Transwell compartment under the Transwell insert was determined as a measure for the transmigration rate.

In order to examine the influence of various ATIII preparations on the transmigration rate of the monocytes, either monocytes or endothelial cells were preincubated for 10 minutes with the test substances and washed or the test substances were added to the medium in the upper Transwell chamber and the test substances were left there during the complete transmigration experiment. In this case addition to the medium during the transmigration is shown.

After a 4 hour transmigration period, the inserts were carefully removed, the cell culture plate was placed for 30 min on ice in order to detach the adhered monocytes and the number of transmigrated monocytes was counted.

FIG. 5: IDAAT activates monocytes and produces a $Ca^{2+}$ signal.

The method used was shown in detail in the description of the example (sequence in the bottom graph: SEQ ID NO: 2).

FIG. 6: IDAAT mediates the binding of TSP-1 to T cells

Cultured human T cells (Jurkat cells) were incubated for 1 hour at room temperature with IDAAT or IDAAT plus TSP-1 at the stated concentrations. TSP-1 bound to the T cells was labelled with the monoclonal PE-conjugated anti-TSP antibody (clone P10) and measured in a flow cytometer. IDAAT mediates the binding of endogenous and exogenously added TSP to T cells.
 a) without TSP-1 addition; without IDAAT addition; anti-TSP antibody PE label
 b) addition of TSP-1 (25 µg/ml); without IDAAT addition; anti-TSP antibody PE label
 c) TSP-1 addition (25 µg/ml); IDAAT addition (1 µg/ml); anti-TSP antibody PE label
 d) TSP-1 addition (25 µg/ml); IDAAT addition (5 µg/ml); anti-TSP antibody PE label
 e) plus/minus TSP-1 (25 µg/ml); IDAAT at increasing concentrations; anti-TSP antibody PE label FIG. 7: IDAAT amplifies the activating effect of fLMF on the oxidative burst of
 a) fLMF dose-dependently triggers the oxidative burst of PMNL
 b) IDAAT increases the oxidative burst triggered by fLMF and, independently of other agonists, is itself able to induce the oxidative burst of PMNL.

FIG. 8: IDAAT inhibits the release of active interleukin 12 by monocytes activated with interferon γ+S. aureus The method used was shown in detail in the description of the example.

FIG. 9: The IL-10 secretion of monocytes activated with S. aureus and interferon γ is increased by IDAAT. Thus IDAAT promotes the secretion of an interleukin which protects against LPS-induced lethality in animal experiments. The method used was carried out analogously to FIG. 8. IL-10 was determined by means of an ELISA.

FIG. 10: (sequence in the figure title: SEQ ID NO:2): The TNF α secretion of monocytes activated with S. aureus and interferon γ is inhibited by the TSP-1 peptide RFYVVMK (SEQ ID NO: 2) (10a). IDAAT increases the inhibitory effect of the TSP-1 peptide (25 µM) (10b): sequence in the 0 µg/mL IDAAT condition: SEQ ID NO: 2; sequence in the 5 µg/mL IDAAT condition: SEQ ID NO: 2; sequence in the 10 µg/mL IDAAT condition: SEQ ID NO: 2). TNF α was determined by means of an ELISA. The method used was carried out analogously to FIG. 8.

FIG. 11: IDAAT inhibits the Arthus reaction in the ear of Balb-C mice
 a) Mouse treated twice intraperitoneally at time 0 and 0+3 hours with 50 µg IDAAT each time. Arthus reaction in the left ear
 b) Mouse treated intraperitoneally twice with control buffer. Arthus reaction in the left ear
 c) BSA-FITC incorporated into the ears as a measure for the Arthus reaction in mice treated with IDAAT or control buffer. Arthus reaction in the left ear.

FIG. 12:
 a) dot plot of the thrombocyte-bacterial association
  A: thrombocytes labelled with PE-conjugated anti-GPIX antibody (Beb 1)
  B: bacteria (S. aureus) labelled with Syto 13
  C: bacteria-thrombocyte associates emitting both fluorescences
 b) S. aureus (Cowan 1)-thrombocyte associates Use of thrombocytes from the patients A.P. and W.K. with gray platelet syndrome. The increase in the rate of association caused by thrombin activation is absent when using gray platelets which lack thrombospondin-1.
 **p<0.005
 *** p<0.0001 c) The S. aureus (Cowan-1)-thrombocyte associate formation is increased by IDAAT. Addition of more TSP-1 leads to a further increase in the number of associates.

FIG. 13: Purified $Ca^{2+}$-containing TSP-1 from human thrombocytes was conjugated with FITC (TSP-1-FITC) and added to gel-filtered platelets. This preparation was incubated for 1 hour at room temperature with IDAAT (2 µg/ml and 5 µg/ml) and measured in a flow cytometer (5000 thrombocytes).

FIG. 14:
 a) 150 µ/ml FITC-conjugated fibrinogen was added to gel-filtered human thrombocytes (50,000/µl) and incubated with collagen at increasing concentrations in the absence or presence of IDAAT (5 µg/ml). The thrombocytes were measured after 30 minutes incubation in a flow cytometer.
 b) 150 µ/ml FITC-conjugated fibrinogen was added to gel-filtered human thrombocytes (50,000/µl), and IDAAT without TSP or with TSP-1 (10 µµg/ml) was added at increasing concentrations. After a 1 hour incubation the thrombocytes were measured in a flow cytometer.

FIG. 15:
 a) IDAAT increases the adhesion of thrombocytes to the adhesion proteins: fibronectin, vitronectia, fibrinogen, thrombospondin-1 and collagen
 b) Comparison of IDAAT and commercial ATIII preparations with regard to their effect on platelet adhesion. The method used was elucidated in detail in the description of the example.

FIG. 16:
 a) The IDAAT-mediated adhesion of thrombocytes to immobilized thrombospondin-1 is completely inhibited by the soluble integrins $\alpha_{IIb}\beta_3$ (5 µg/ml) and $\alpha_V\beta_3$ (5 µg/ml). The method used was elucidated in detail in the description of the example.
 b) The IDAAT-mediated adhesion of thrombocytes to immobilized vitronectin is partially inhibited by the soluble integrins $\alpha_{IIb}\beta_3$ (5 µg/ml) and $\alpha_V\beta_3$ (5 µg/ml). The method used was elucidated in detail in the description of the example.

FIG. 17: The IDAAT-mediated adhesion of thrombocytes to immobilized TSP-1 is completely inhibited by the CD36-specific antibody clone 37 when the Fc receptor is simultaneously blocked by IV.3. Blockade of the Fc receptor alone has no effect. The method used was elucidated in detail in the description of the example.

FIG. 18: The IDAAT-mediated thrombocyte adhesion was carried out using hirudin (20 U/ml) anticoagulated platelet-rich plasma. The method used was elucidated in detail in the description of the example.

FIG. 19: The IDAAT-mediated adhesion of thrombocytes to TSP-1 is dependent on divalent ions.

EDTA (5 mM) completely inhibits this IDAAT effect. 1 mM $Ca^{2+}$ considerably increases this effect of IDAAT. The method used was elucidated in detail in the description of the example.

FIG. 20: Addition of soluble TSP-1 dose-dependently inhibits the adhesion of thrombocytes to collagen, whereas IDAAT which immobilizes TSP-1, dose-dependently increases the adhesion of thrombocytes to collagen. The method used was elucidated in detail in the description of the example.

FIG. 21: The addition of monocytes (100/µl) to thrombocytes (300,000/µl) increases the adhesion of thrombocytes to TSP-1, whereas the addition of erythrocytes (20,000/µl)

has an inhibitory effect. The method used was elucidated in detail in the description of the example.

FIG. 22: The IDAAT-induced thrombocyte adhesion was inhibited by the inhibitors of PI-3 kinase Wortmannin (20 nM) and LY294002 (50 µm). For this purpose Wortmannin and LY294002 were preincubated for 10 minutes before adding IDAAT.

FIG. 23: IDAAT mediates thrombospondin-mediated thrombocyte aggregation Thrombocyte aggregation was carded out according to Born 1962. TSP-1 (25 µg/ml) was pipetted into an aggregation cuvette containing gel-filtered platelets (200,000/µl) in Hepes-Tyrode buffer pH 7.4 containing 100 µg/ml fibrinogen. Soluble TSP-1 does not initiate aggregation. Addition of IDAAT led to a weak aggregation reaction. Simultaneous addition of IDAAT and soluble TSP-1 led to a pronounced aggregation.

FIG. 24: IDAAT mediates the microparticle formation of thrombocytes Gel-filtered platelets (50,000/µl) were activated with the TSP-1 peptide RFYVVMWK (SEQ ID NO: 2) (40 µM) and IDAAT was added at increasing concentrations. After 30 minutes incubation platelets and the microparticles formed from the platelets were labelled with anti GPIX-PE and the number of microparticles generated per 5000 counted platelets was measured in a low cytometer.

FIG. 25: IDAAT mediates TSP-1 binding to endothelial cells

The method used was elucidated in detail in the description of the example. IDAAT increases the TSP-1 binding to endothelial cells.

FIG. 26: IDAAT increases the binding of thrombocytes to vitronectin-coated latex beads. The method used was elucidated in detail in the description of the example.

FIG. 27:
a) IDAAT is composed of polymeric ATIII which is shown by the rotary shadowing electron microscopy method
b) conventional ATIII is composed of monomeric globular molecules; electron micrograph after rotary evaporation
c) IDAAT (1 mg/ml) and TSP-1 (200 µg/ml) were incubated together for 1 hour at room temperature. IDAAT and TSP-1 together form large associates; electron micrograph after rotary evaporation
d) commercial ATIII (1 mg/ml) and TSP-1 (200 µg/ml) were incubated together for 1 hour at room temperature. Commercial ATIII and TSP-1 did not react with one another; electron micrograph after rotary evaporation FIG. 28: IDAAT binds directly to CD4

Recombinant CD4 (1 µg/100 µl/well) was bound to the bottom of an ELISA plate (Nunc-Maxisorb). The plate was washed thoroughly with PBS pH 7.4, 0.5% Tween 20 and unoccupied sites on the plastic surface were blocked for 1 hour at room temperature with 3% BSA. The plate was washed again and subsequently IDAAT or commercial ATIII was added at increasing concentrations of 0-5 µg/ml for 1 hour at room temperature. The ATIII solutions were removed, the plate was thoroughly washed and incubated with a polyclonal monospecific antibody against ATIII from the rabbit (DAKO, Hamburg) at a dilution of 1:15000 in PBS, 1% NGS (normal goat serum). The plate was washed again and subsequently incubated with an affinity-purified antibody from the goat against rabbit IgG which was conjugated with peroxidase (BIORAD, Munich) at a dilution of 1:3000. The plate was again washed several times and substrate solution (100 µl/well) (20 mg ortho-phenyl-diamine, 5% $H_2O_2$ in a buffer consisting of 12.15 ml, 0.1 M citric acid and 12.85 ml 0.2 M $Na_2HPO_4$ plus 25 ml distilled water) was added.

The absorbance at 405 nm measured in an ELISA photometer is a measure for the amount of bound antithrombin. The reaction was stopped by adding 50 µl/well 4 N $H_2SO_4$ to each well and the absorbance was measured at 490 nm. The reaction clearly shows that IDAAT not only mediates TSP-1 but can also bind directly to CD4.

FIG. 29: IDAAT binds directly to HIV-GP120

Recombinant HIV-GP120 (1 µg/100 µl/well) was bound to the bottom of an ELISA plate (Nunc-Maxisorb). The plate was washed thoroughly with PBS pH 7.4, 0.05% Tween 20 and unoccupied sites on the plastic surface were blocked for 1 hour at room temperature with 3% BSA. The plate was washed again and subsequently IDAAT or commercial ATIII was added at increasing concentrations of 0-5 µg/ml for 1 hour at room temperature. The ATIII solutions were removed, the plate was thoroughly washed and incubated with a polyclonal monospecific antibody against ATIII from the rabbit (DAKO, Hamburg) at a dilution of 1:15000 in PBS, 1% NGS (normal goat serum). The plate was washed again and subsequently incubated with an affinity-purified antibody from the goat against rabbit IgG which was conjugated with peroxidase (BIORAD, Munich) at a dilution of 1:3000. The plate was again washed several times and substrate solution (100 µl/well) (20 mg ortho-phenyl-diamine, 5% $H_2O_2$ in a buffer consisting of 12.15 ml, 0.1 M citric acid and 12.85 ml 0.2 M $Na_2HPO_4$ plus 25 ml distilled water) was added.

The absorbance at 405 nm measured in an ELISA photometer is a measure for the amount of bound antithrombin The reaction was stopped by adding 50 µl/well 4 N $H_2SO_4$ to each well and the absorbance was measured at 490 nm. The reaction clearly shows that IDAAT not only mediates TSP-1 but can also bind directly to HIV-GP120.

FIG. 30: IDAAT binds directly to thrombospondin

Purified thrombospondin-1 (1 µg/100 µl/well) was bound to the bottom of an ELISA plate (Nunc-Maxisorb). The plate was washed thoroughly with PBS pH 7.4, 0.05% Tween 20 and unoccupied sites on the plastic surface were blocked for 1 hour at room temperature with 3% BSA. The plate was washed again and subsequently IDAAT or commercial ATIII was added at increasing concentrations of 0-5 µg/ml for 1 hour at room temperature. The ATIII solutions were removed, the plate was thoroughly washed and incubated with a polyclonal monospecific antibody against ATIII from the rabbit (DAKO, Hamburg) at a dilution of 1:15000 in PBS, 1% NGS (normal goat serum). The plate was washed again and subsequently incubated with an affinity-purified antibody from the goat against rabbit IgG which was conjugated with peroxidase (BIORAD, Munich) at a dilution of 1:3000. The plate was again washed several times and substrate solution (100 µl/well) (20 mg ortho-phenyl-diamine, 5% $H_2O_2$ in a buffer consisting of 12.15 ml, 0.1 M citric acid and 12.85 ml 0.2 M $Na_2HPO_4$ plus 25 ml distilled water) was added.

The absorbance at 405 nm measured in an ELISA photometer is a measure for the amount of bound antithrombin. The reaction was stopped by adding 50 µl/well 4 N $H_2SO_4$ to each well and the absorbance was measured at 490 inn. The reaction clearly shows that IDAAT can directly bind to TSP-1.

FIG. 31: IDAAT binds directly to vitronectin (active form)

Vitronectin (1 µg/100 µl/well) was bound to the bottom of an ELISA plate (Nunc-Maxisorb). The plate was washed thoroughly with PBS pH 7.4, 0.05% Tween 20 and unoccupied sites on the plastic surface were blocked for 1 hour at room temperature with 3% BSA. The plate was washed again and subsequently IDAAT or commercial ATIII was added at increasing concentrations of 0-5 µg/ml for 1 hour at room temperature The ATIII solutions were removed, the plate was thoroughly washed and incubated with a polyclonal monospecific antibody against ATIII from the rabbit (DAKO, Hamburg) at a dilution of 1:15000 in PBS, 1% NGS (normal goat serum). The plate was washed again and subsequently incubated with an affinity-purified antibody from the goat against rabbit IgG which was conjugated with peroxidase (BIORAD, Munich) at a dilution of 1:3000. The plate was again washed several times and substrate solution (100 µl/well) (20 mg ortho-phenyl-diamine, 5% $H_2O_2$ in a buffer consisting of 12.15 ml, 0.1 M citric acid and 12.85 ml 0.2 M $Na_2HPO_4$ plus 25 ml distilled water) was added. The absorbance at 405 nm measured in an ELISA photometer is a measure for the amount of bound antithrombin. The reaction was stopped by adding 50 µl/well 4 N $H_2SO_4$ to each well and the absorbance was measured at 490 inn. The reaction clearly shows that IDAAT can directly bind to active vitronectin.

Preparation of IDAAT:

EXAMPLE 1

Antithrombin III which is non-functional and not activated in the described sense was obtained either from Calbiochem, Sigma, Enzyme Research Laboratories, Pharmacia & Upjohn, Aventis, Baxter or Grifols or purified from human plasma. The antithrombin preparations were rebuffered against phosphate-buffered saline (PBS) pH 7.4. 348 µg pure antithrombin was made up to a volume of 1 ml with PBS pH 7.4 and 0.1 mM EDTA and the solution was cooled on ice. Cold NaOCl (832 µg) was added in a volume of 10 µl and the preparation was incubated for 10 minutes on ice. The reaction was terminated by immediate gel filtration at 4° C. on Sephadex G25 (PD10 columns).

EXAMPLE 2

Commercial, non-activated antithrombin III was rebuffered against PBS pH 8.0. 50 µg neutrophilic granulocyte elastase (HNE) (human, dissolved in 50 µl buffer) was added to 500 µg pure antithrombin III and the mixture (500 µl volume) was incubated for 16 hours at 37° C. The reaction was terminated with 1 mM (final concentration) phenylmethylsulfonyl fluoride (PMSF) and the antithrombin III was rebuffered against PBS/0.1 mM EDTA pH 7.4 using the Centricon method. It was subsequently oxidized with NaOCl as described in example 1.

EXAMPLE 3

Commercial non-activated antithrombin III was rebuffered against PBS pH 8.0. 12.4 pg matrix metalloproteinase 2 (MMP-2) (dissolved in 0.9% NaCl) was mixed with 500 µg pure antithrombin III in 25 mM Tris/HCl/30 mM NaCl/10 mM $Ca^{2+}$ buffer. In order to activate the M-2 it was pretreated for 2 hours at room temperature with 1 mM APMA (4-amino phenylmercuric acetate). The mixture (500 µl volume) was incubated for 16 hours at 37° C. The antithrombin III was rebuffered against PBS pH 7.4 using the Centricon method.

EXAMPLE 4

Commercial non-activated antithrombin III was rebuffered against PBS pH 8.0. 200 µg pure antithrombin III was incubated for 1 hour at room temperature with defensin 2 (HNP-2, dissolved in 0.9% NaCl, final concentration 10 µM) in PBS pH 8.0.

REFERENCES

1. Armant M, Avice M N, Hermann P, Rubio M, Kiniwa M, Delespesse G, Sarfati M: CD47 ligation selectively down-regulates human interleukin 12 production. J.Exp.Med. 190: 1175-1182, 1999
2. Asch A S, Liu l, Briccetti F M, Barnwell J W, Kwakye-Berko F, Dokun A, Goldberger J, Pernambuco M: Analysis of CD36 binding domains: ligand specificity controlled by dephosphorylation of an ectodomain. Science 262: 1436-1440, 1993
3. Barnes D A, Tse J, Kaufhold M, Owen M, Hesseigesser J, Strieter R, Horuk R, Perez H D: Polyclonal antibody directed against human RANTES ameliorates disease in the Lewis rat adjuvant-induced arthritis model. J. Clin. Invest 101: 2910-29199, 1998
4. Born G V: [The blood platelets in thrombogenesis. The mechanism and inhibition of the aggregation of blood platelets]. Actual. Pharmacol. (Paris) 18: 1732-1965
5. Bornstein P, Devarayalu S, Li P, Disteche C M, Framson P: A second thrombospondin gene in the mouse is similar in organization to thrombospondin 1 but does not respond to serum. Proc. Natl. Acad. Sci. USA 88: 8636-8640, 1991
6. Bornstein P: Thrombospondins: structure and regulation of expression [published erratum appears in FASEB J 1993 January; 7(1):237]. FASEB J. 6: 3290-3299, 1992
7. Chung J. Gao A G, Frazier W A: Thrombospondin acts via integrin-associated protein to activate the platelet integrin alphaIIbbeta 3. J. Biol. Chem. 272: 14740-14746, 1997
8. Chung J, Wang X Q, Lindberg F P, Frazier W A: Thrombospondin-1 acts via IAP/CD47 to synergize with collagen in alpha2betaI-mediated platelet activation. Blood 94: 642-6489 1999
9. Crawford S E, Stellmach V, Murphy-Ullrich J E, Ribeiro S M, Lawler J, Hynes R O, Boivin G P, Bouck N: Thrombospondin-1 is a major activator of TGF-betaI in vivo. Cell 93: 1159-1170, 1998
10. Crombie R, Silverstein R L, MacLow C, Pearce S F A, Nachman R L, Laurence J: Identification of a CD36-related thrombospondin 1 binding domain in HIV-1 envelope glycoprotein gp120: relationship to HIV-1 specific inhibitory factors in human saliva. Exp. Med. 187: 25-35, 1998
11. Dardik R, Lahav J: Functional changes in the conformation of thrombospondin-1 during complexation with fibronectin or heparin. Exp. Cell. Res. 248: 407-414, 1999
12. Demeure C E, Tanaka H, Mateo V, Rubio M, Delespesse G, Sarfati M: CD47 engagement inhibits cytokine production and maturation of human dendritic cells. J. Immunol. 164: 2193-2199, 2000
13. Dickneite G, Paques E P: Reduction of mortality with antithrombin 111 in septicemic rats: a study of *Klebsiella pneumoniae* induced sepsis. Thromb. Haemost. 69: 98-102, 1993
14. Dörmann D, Kardoeus J, Zimmermann R E, Kehrel B: Flow cytometric analysis of agonist-induced annexin V, factor Va and factor Xa binding to human platelets. Platelets 9: 171-1771, 1998
15. Fadok V A, Bratton D L, Konowal A, Freed P W, Westcott J Y, Henson P M: Macrophages that have ingested apoptotic cells in vitro inhibit proinflammatory cytokine production through autocrine/paracrine mechanisms involving TGF-beta, PGE2 and PAF. J. Clin Invest 101: 890-8982, 1998
16. Galvin N J, Dixit V M, O'Rourke K M, Santoro S A, Giant G A, Frazier W A: Mapping of epitopes for monoclonal antibodies against human platelet thrombospondin with electron microscopy and high sensitivity amino acid sequencing. J. Cell Biol. 101: 1434-1441, 1985
17. Geiser A G, Letterio J J, Kulkarni A B, Karlsson S, Roberts A B, Sporn M B: Transforming growth factor beta 1 (TGF beta 1 controls expression of major histocompatibility genes in the postnatal mouse: aberrant histocompatibility antigen expression in the pathogenesis of the TGF beta 1 null mouse phenotype. Proc. Natl. Acad. Sci. USA 90:9944-9948, 1993
18. Higazi A A, Upson R H, Cohen R L, Manuppello J, Bognacki J, Henkin J, McCrae K R, Kounnas M Z, Strickland D K, Preissner K T, Lawier J, Cines D B: Interaction of single-chain urokinase with its receptor induces the appearance and disappearance of binding epitopes within the resultant complex for other cell surface proteins. Blood 88: 542-5511, 1996
19. Iruela-Arispe M L; Lombardo M, Krutzsch H C, Lawler J, Roberts D D: Inhibition of angiogenesis by thrombospondin-1 is mediated by 2 independent regions within the type 1 repeats. Circulation 100: 1423-14311, 1999
20. Jander R, Troyer D, Rauterberg J: A collagen-like glycoprotein of the extracellular matrix is the undegraded form of type VI collagen. Biochemistry 23: 3675-3681, 1984
21. Jimenez B, Volpert O V, Crawford S E, Febbraio M, Silverstein R L, Bouck N: Signals leading to apoptosis-dependent inhibition of neovascularization by thrombospondin-1, Nat.Med. 6: 41-48, 2000
22. Kainoh M, Imai R, Umetsu T, Hattori M, Nishio S: Prostacyclin and beraprost sodium as suppressors of activated rat polymorphonuclear leucocytes. Biochem. Pharmacol. 39: 477-4841, 1990
23. Kaplan H J, Leibole M A, Tezei T, Ferguson T A: Fas ligand (CD95 ligand) controls angiogenesis beneath the retina. Nat. Med. 5: 292-297, 1999
24. Kappe S, Bruderer T, Gantt S, Fujioka H, Nussenzweig V, Menard R: Conservation of a gliding motility and cell invasion machinery in Apicomplexan parasites. J. Cell Biol. 147: 937-9441, 1999
25. Kehrel B, Balleisen L, Kokott t, Mesters R, Stenzinger W, Clemetson K J, van de L J: Deficiency of intact thrombospondin and membrane glycoprotein Ia in platelets with defective collagen-induced aggregation and spontaneous loss of disorder. Blood 71: 1074-10787, 1988
26. Kehrel B, Kronenberg A, Schwippert B, Niesing-Bresch D, Niehues U, Tschope D, van de L J, Clemetson K J: Thrombospondin binds normally to glycoprotein IIIb deficient platelets. Biochem. Biophys. Res. Commun. 179: 985-991, 1991
27. Kehrel B, Flicker E: Thrombospondin in Pathophysiology—Thrombospondin in Relation with Disease Processes, in Lahav J (ed): Thrombospondin. Boca Raton, CRC Press, 1993, pp 199-207
28. Kehrel B, Flicker E, Wigbels B Osterfeld M, van de L J, Luscher E F: Thrombospondin measured in whole blood—an indicator of platelet activation. Blood Coagul. Fibrinolysis 7: 202-205, 1996
29. Kehrel B, Wierwille S, Clemetson K J, Anders O, Steiner M, Knight C G, Farndale R W, Okuma M, Barnes M J: Glycoprotein VI is a major Collagen receptor for platelet activation: it recognizes the platelet-activating quaternary structure of collagen, whereas CD36, glycoprotein IIb/IIIa and Willebrand factor do not. Blood 91: 491-4991, 1998
30. Kielbassa K, Schmitz C, Gerke V: Disruption of endothelial microfilaments selectively reduces the transendothelial migration of monocytes. Exp. Cell Res. 243; 129-141, 1998
31. Kronenberg A, Grahl H, Kehrel B: Human platelet CD36 (BPIIIb, GPIV) binds to cholesteryl-hemisuccinate and can be purified by a simple two-step method making use of this property. Thromb. Haemost. 79: 1021-1024, 1998
32. Kulkarni A B, Huh C G, Becker D, Geiser A, Lyght M, Flanders K C, Roberts A B, Sporn M B, Wark J M, Karlsson S: Transforming growth factor beta 1 null mutation in mice causes excessive inflammatory response and early death. Proc. Natl. Acad. Sci. USA 90: 770-774, 1993
33. Kulkarni A B, Karisson S: Inflammation and TGF beta 1: lessons from the TGF beta 1 null mouse. Res. Immunol. 148: 453-456, 1997
34. Lawler J, Hynes R O: The structure of human thrombospondin, an adhesive glycoprotein with multiple calcium-binding sites and homologies with several different proteins. J. Cell Biol. 103: 1635-1648, 1986
35. Lawler J: The structural and functional properties of thrombospondin. Blood 67: 1197-1209, 1986
36. Lawler J, Weinstein R, Hynes R O: Cell attachment to thrombospondin: the role of ARG-GLY-ASP, calcium and integrin receptors. J. Cell Biol. 107: 2351-2361, 1988
37. Lawler J, Duquette M, Urry L, McHenry K, Smith T F: The evolution of the thrombospondin gene family. J. Mol. Evol. 36: 509-516, 1993
38. Lawler J, Sunday M, Thibert V, Duquette M, George E L, Rayburn H, Hynes R O: Thrombospondin-1 is required for normal murine pulmonary homeostasis and its absence causes pneumonia J. Clin. Invest 101: 982-9921, 1998
39. Letterio J J, Geiser A G, Kulkarni A B, Dang H, Kong L, Nakabayashi T, Mackall C L, Gress R E, Roberts A B: Autoimmunity associated with TGF-beta 1 deficiency in mice is dependent on MHC class 11 antigen expression. J. Clin. Invest 98: 2109-2119, 1996
40. Leung L L, Li W X, McGregor J L, Albrecht G, Howard R J: CD36 peptides enhance or inhibit CD36-thrombospondin binding. A two-step process of ligand-receptor interaction. J. Biol. Chem. 267: 18244-18250, 1992
41. Li D Q, Lundberg F, Ljungh A: Binding of von Willebrand factor by coagulase-negative *staphylococci*. J. Med. Microbiol. 49: 217-2259, 2000
42. Lindstedt K A, Kokkonen J O, Kovanen P T: Soluble heparin proteoglycans released from stimulated mast cells induce uptake of low density lipoproteins by macrophages via scavenger receptor-mediated phagocytosis. J. Lipid Res. 33: 65-75, 1992
43. Mateo V, Lagneaux L, Bron D, Biron G, Armant M, Delespesse G, Sarfati M: CD47 ligation induces caspase-independent cell death in chronic lymphocytic leukemia. Nat. Med. 5: 1277-1284, 1999
44. Munjai I D, Crawford D R, Blake D A, Sabet M D, Gordon S R: Thrombospondin: biosynthesis, distribution and changes associated with wound repair in corneal endothelium [published erratum appears in Eur. J. Cell Biol. 1991 August 55(2): IV]. Eur. J. Cell Biol. 52: 252-263, 1990
45. Murphy-Ullrich J E, Gurusiddappa S, Frazier W A, Hook M: Heparin-binding peptides from thrombospondins 1 and 2 contain focal adhesion-labilizing activity J. Biol. Chem. 268: 26784-26789, 1993
46. Nakamura T, Amano A, Nakagawa I, Hamada S: Specific interactions between *Porphyromonas gingivalis fimbriae* and human extracellular matrix proteins. FEMS Microbiol. Lett. 175: 267-272, 1999
47. Patthy L: Detecting distant homologies of mosaic proteins. Analysis of the sequences of thrombomodulin, thrombospondin complement components C9, C8 alpha and C8 beta, vitronectin and plasma cell Membrane glycoprotein PC-1. J. Mol. Biol. 202: 689-6969, 1988
48. Roberts D D, Sherwood J A, Spitalnik S L, Panton L J, Howard R J, Dixit V M, Frazier W A, Miller L H, Ginsburg V: Thrombospondin binds falciparum malaria parasitized erythrocytes and may mediate cytoadherence. Nature 318: 64-66, 1985
49. Roberts D D: Regulation of tumor growth and metastasis by thrombospondin-1, FASEB J. 10: 1183-1191, 1996

50. Santoro S A, Zutter M M, Wu Je, Staatz W D, Saelman E U, Keely P J: Analysis of collagen receptors. Methods Enzymol. 245: 147-1839, 1994
51. Savill J, Hogg N, Ren Y, Haslett C: Thrombospondin cooperates with CD36 and the vitronectin receptor in macrophage recognition of neutrophils undergoing apoptosis. J. Clin. Invest. 90: 1513-1522, 1992
52: Schultz-Cherry S, Murphy-Ullrich J E: Thrombospondin causes activation of latent transforming growth fractor-beta secreted by endothelial cells by a novel mechanism [published erratum appears in J. Cell Biol. 1993 September; 122(5): following 1143]. J. Cell. Biol. 122: 923-932, 1993
53. Schultz-Cherry S, Lawier J, Murphy-Ullrich J E: The type 1 repeats of thrombospondin 1 activate latent transforming growth factor-beta. J. Biol. Chem. 269: 26783-26788, 1994
54. Shafiee A, Penn J S, Krutzsch H C, Inman J K, Roberts D D, Blake D A: Inhibition of retinal angiogenesis by peptides derived from thrombospondin-1. Invest Ophthalmol. Vis. Sci. 41: 2378-23881, 2000
55. Shull M M; Ormsby I, Kier A B, Pawlowski S, Diebold R J, Yin M, Allen R, Sidman C, Proetzei G, Calvin D: Targeted disruption of the mouse transforming growth factor-beta 1 gene results in multifocal inflammatory disease. Nature 359: 693-699, 1992
56. Silverstein R L, Nachman R L: Thrombospondin-plasminogen interactions: modulation of plasmin Generation. Semin. Thromb. Hemost. 13: 335-342, 1987
57. Silverstein R L, Nachman R L, Pannell R, Gurewich V, Harpel P C: Thrombospondin forms complexes with single-chain and two-chain forms of urokinase [published erratum appears in J. Biol. Chem. 15 Sep. 1990 265(26): 16025]. J. Biol. Chem. 265: 11289-11294, 1990
58. Sozzani S, Molino M, Locati M, Luini W, Cerletti C, Vecchi A, Mantovani A: Receptor-activated calcium influx in human monocytes exposed to monocyte chemotactic protein-1 and related cytokines. J. Immunol. 150: 1544-15531, 1993
59. Stangl K, Dschietzig T, Alexiou K, Brunner F: Antithrombin increases pulmonary endothelins: inhibition by heparin and Ca2+ channel antagonism. Eur. J. Pharmacol. 370: 57-61, 1999
60. Steinhauser M L, Hogaboam C M, Lukacs N W, Strieter R M, Kunkel S L: Multiple roles for IL-12 in a model of actate septic peritonitis J. Immunol. 162: 5437-5443, 1999
61. Stern M, Savill J, Haliett C: Human monocyte-derived macrophage phagocytosis of senescent eosinophils undergoing apoptosis. Mediation by alpha v beta 3/CD/36/thrombospondin recognition mechanism and lack of phlogistic response. Am. J. Pathol. 149: 911-921, 1996
62. Sulaiman I M, Lal A A, Arrowood M T, Xiao L: Bialielic polymorphism in the intron region of beta-tubulin gene of *Cryptosporidium parasites*. J. Parasitol. 85: 154-157, 1999
63. Uchiba M, Okajima K, Murakami K, Okabe H, Takatsuki K: Attenuation of endotoxin-induced pulomoary vascular injury by antithrombin III. Am. J. Physiol 270: L921-L930, 1996
64. Watkins S C, Lynch G W, Kane L P, Slayter H S: Thrombospondin expression in traumatized skeletal muscle. Correlation of appearance with post-trauma regeneration. Cell Tissue Res. 261: 73-84t i990
65. Wengelnik K, Spaccapelo R, Naitza S, Robson K J, Janse C J, Bistoni F, Waters A P, Crisanti A: The A-domain and the thrombospondin-related motif of *Plasinodium falciparum* TRAP are implicated in the invasion process of mosquito salivary glands. EMBO J. 18: 5195-5204, 1999
66. Yamauchi T. Umeda F, Inoguchi T, Nawata H: Antithrombin III stimulates prostacyclin production by cultured aortic endothelial cells. Biochem. Biophys. Res. Commun. 163: 1404-1411, 1989
67. Yatohgo T, Izumi M, Kashiwagi H, Hayashi M: Novel purification of vitronectin from buman plasma by heparin affinity chromatography. Cell Struct. Funct. 13: 281-292, 1988
68. Yehualaeshet T, O'Connor R, Green-Johnson J, Mai S, Silverstein R, Murphy-Ullrich J E, Khalii N: Activation of rat alveolar macrophage-derived latent transforming growth factor beta-1 by plasmin requires interaction with thrombospondin-1 and its cell surface receptor, CD36. Am. J. Pathol. 155: 841-851, 1999

The invention claimed is:

1. Pharmaceutical preparation containing oxidized antithrombin III (IDAAT) wherein the said antithrombin III (IDAAT) mediates interaction with proteins selected from the group consisting of thrombospondin, vitronectin, CD36, oxLDL, $\alpha_{IIb}\beta$-integrin and $\alpha_V\beta3$-integrin and wherein the IDAAT is oxidized by means of hypochlorite.

2. Pharmaceutical preparation as claimed in claim 1, characterized in that it contains recombinant IDAAT.

3. Pharmaceutical preparation as claimed in claim 1, characterized in that
   it contains additional pharmaceutically acceptable auxiliary substances or/and excipients.

4. Pharmaceutical preparation as claimed in claim 1, characterized in that
   it is formulated for local, intradermal, superficial, intraperitoneal, Intravenous, oral or intramuscular administration or it is administered by means of vesicles.

5. Pharmaceutical preparation as claimed in claim 1, characterized in that it contains additional substances selected from the group consisting of antibiotics or interaction partners of IDAAT in the body.

6. Pharmaceutical preparation as claimed in claim 1, characterized in that the oxidation by means of hypochlorite is an in vitro oxidation.

* * * * *